US005789224A

United States Patent [19]

Gelfand et al.

[11] Patent Number: 5,789,224

[45] Date of Patent: *Aug. 4, 1998

[54] RECOMBINANT EXPRESSION VECTORS AND PURIFICATION METHODS FOR THERMUS THERMOPHILUS DNA POLYMERASE

[75] Inventors: David H. Gelfand, Oakland; Frances C. Lawyer, Davis; Susanne Stoffel, El Cerrito, all of Calif.

[73] Assignee: Roche Molecular Systems, Inc., Branchburg, N.J.

[*] Notice: The term of this patent shall not extend beyond the expiration date of Pat. No. 5,618,711.

[21] Appl. No.: 459,383

[22] Filed: Jun. 2, 1995

Related U.S. Application Data

[62] Division of Ser. No. 384,490, Feb. 6, 1995, Pat. No. 5,618,711, which is a continuation of Ser. No. 148,133, Nov. 2, 1993, abandoned, which is a continuation of Ser. No. 880,478, May 6, 1992, abandoned, which is a continuation of Ser. No. 455,967, Dec. 22, 1989, abandoned, which is a continuation-in-part of Ser. No. 143,441, Jan. 12, 1988, abandoned, which is a continuation-in-part of Ser. No. 63,509, Jun. 17, 1987, Pat. No. 4,889,818, which is a continuation-in-part of Ser. No. 899,241, Aug. 22, 1986, abandoned.

[51] Int. Cl.$^6$ ............................................. C12N 9/12
[52] U.S. Cl. ............................................. 435/194
[58] Field of Search ............................ 435/194; 536/23.2

[56] References Cited

U.S. PATENT DOCUMENTS

| 4,683,195 | 7/1987 | Mullis et al. | 435/6 |
| 4,683,202 | 7/1987 | Mullis | 435/91 |
| 4,889,818 | 12/1989 | Gelfand et al. | 435/194 |
| 5,079,352 | 1/1992 | Gelfand et al. | 536/27 |
| 5,192,674 | 3/1993 | Oshima et al. | 435/194 |

FOREIGN PATENT DOCUMENTS

| 0258017 | 3/1988 | European Pat. Off. |
| 0359006 | 8/1989 | European Pat. Off. |
| 8906691 | 7/1989 | WIPO |

OTHER PUBLICATIONS

Sakaguchi and yajima, May, 1974, "Thermophilic and Stable DNA Polymerase From Thermus Thermophilus" Fed. Proceeds. 33(5):1492 (Abstract No. 1519).

Johnson et al., November, 1985, "Isolation of the Gene Encoding Yeast DNA Polymerase I" Cell 43:369–377.

Ruttimann et al., 1985, "DNA Polymerases From the Extremely Thermophilic Bacterium Thermus Thermophilus HB–8" Eur. J. Biochem. 149:41–46.

Bechtereva et al., 1989, "DNA Sequencing With Thermostable Tet DNA Polymerase From Thermus Thermophilus" Nucleic Acids Research 17(24):10507.

Lawyer et al., Apr., 1989, "Isolation, Characterizations, and Expression in *Escherichia coli* of the DNA Polymerase Gene from Thermus Aquaticus" J. Biological Chemistry 264(11):6427–6437.

Sambrook et al., Molecular Cloning: Laboratory Manual, second edition, vol. 2, Cold Spring Harbor Laboratory Press, N.Y. (1989) pp. 13.3–13.10 "Sequencing Techniques and Strategies".

Chien et al., Sep., 1976, "Deoxyribonucleic Acid Polymerase From the Extreme Thermophilie Thermus aquaticus" J. Bacteriology 127(3):1550–1557.

Stoesz and Lumry, 1978, "Refolding Transition of alpha–Chymotrypsin: pH and Salt Dependence" Biochemistry 17(18):3693–3699.

Hon–nami and Oshima, 1979, "Denaturation of Thermophilic Ferricytochrome c–552 by Acid, Guanidine Hydrochloride, and Heat" Biochemistry 18(25):5693–5697.

Kaledin et al., Apr., 1980, "Isolation and Properties of DNA Polymerase From Extremely Thermophilic Bacterium Thermus aquaticus YT1" Biokhimiya 45(4):644–651.

Elie et al., 1989, "Thermostable DNA Polymerase From the Archaebacterium Sulfolobus Acidocaldrius Purification, Characterization and Immunological Properties" Eur. J. Biochem. 178:619–626.

Finnzymes Oy Tth DNA Polymerase Produce Sheets (no date available).

Toyobo Co., Ltd. Tth DNA Polymerase Product Sheets, 1988.

USB Tth DNA Polymerase Product Sheet, 1989.

*Primary Examiner*—Keith D. Hendricks
*Attorney, Agent, or Firm*—George W. Johnston; Dennis P. Tramaloni; Douglas A. Petry

[57] ABSTRACT

Recombinant DNA sequences encoding the DNA polymerase activity of *Thermus thermophilus* can be used to construct recombinant vectors and transformed host cells for production of the activity. *T. thermophilus* DNA polymerase is an ~94 kDa protein especially useful in the DNA amplification procedure known as the polymerase chain reaction.

5 Claims, No Drawings

RECOMBINANT EXPRESSION VECTORS AND PURIFICATION METHODS FOR THERMUS THERMOPHILUS DNA POLYMERASE

CROSS-REFERENCE

This application is a divisional, of application Ser. No. 08/384,490 filed Feb. 6, 1995, now U.S. Pat. No. 5,618,711, which is a continuation of Ser. No. 08/148,133, filed Nov. 2, 1993 now abandoned, which is a continuation of U.S. Ser. No. 07/880,478, filed May 6, 1992, now abandoned, which is a continuation of U.S. Ser. No. 07/455,967, filed Dec. 22, 1989, now abandoned, which is a continuation-in-part of U.S. Ser. No. 07/143,441, filed Jan. 12, 1988, now abandoned, which is a continuation-in-part of U.S. Ser. No. 07/063,509, filed Jun. 17, 1987, which issued as U.S. Pat. No. 4,889,818, which is a continuation-in-part of U.S. Ser. No. 06/899,241, filed Aug. 22, 1986, now abandoned.

BACKGROUND OF THE INVENTION

1. Field of the Invention

The present invention relates to a purified, thermostable DNA polymerase purified from *Thermus thermophilus* and recombinant means for producing the enzyme. Thermostable DNA polymerases are useful in many recombinant DNA techniques, especially nucleic acid amplification by the polymerase chain reaction (PCR).

2. Background Art

Extensive research has been conducted on the isolation of DNA polymerases from mesophilic microorganisms such as *E. coli*. See, for example, Bessman et al., 1957, *J. Biol. Chem.* 233:171–177 and Buttin and Kornberg, 1966, *J. Biol. Chem.* 241:5419–5427.

Much less investigation has been made on the isolation and purification of DNA polymerases from thermophiles such as *Thermus thermophilus*. Kaledin et al., 1980, *Biokhymiya* 45:644–651 disclose a six-step isolation and purification procedure of DNA polymerase from cells of *T. aquaticus* YT-1 strain. These steps involve isolation of crude extract, DEAE-cellulose chromatography, fractionation on hydroxyapatite, fractionation on DEAE-cellulose, and chromatography on single-strand DNA-cellulose. The pools from each stage were not screened for contaminating endo- and exonuclease(s). The molecular weight of the purified enzyme is reported as 62,000 daltons per monomeric unit.

A second purification scheme for a polymerase from *Thermus aquaticus* is described by Chien et al., 1976, *J. Bacteriol.* 127:1550–1557. In this process, the crude extract is applied to a DEAE-Sephadex column. The dialyzed pooled fractions are then subjected to treatment on a phosphocellulose column. The pooled fractions are dialyzed and bovine serum albumin (BSA) is added to prevent loss of polymerase activity. The resulting mixture is loaded on a DNA-cellulose column. The pooled material from the column is dialyzed and analyzed by gel filtration to have a molecular weight of about 63,000 daltons and by sucrose gradient centrifugation of about 68,000 daltons.

The use of thermostable enzymes, such as those prepared by Chien et al. and Kaledin et al., to amplify existing nucleic acid sequences in amounts that are large compared to the amount initially present was described in U.S. Pat. Nos. 4,683,195 and 4,683,202, which describe the PCR process. Primers, template, nucleoside triphosphates, the appropriate buffer and reaction conditions, and a polymerase are used in the PCR process, which involves denaturation of target DNA, hybridization of primers, and synthesis of complementary strands. The extension product of each primer becomes a template for the production of the desired nucleic acid sequence. The patents disclose that, if the polymerase employed is a thermostable enzyme, then polymerase need not be added after every denaturation step, because heat will not destroy the polymerase activity.

European Patent Publication No. 258,017 and PCT Publication No. 89/06691 describe the isolation and recombinant expression of an ~94 kDa thermostable DNA polymerase from *Thermus aquaticus* and the use of that polymerase in PCR. Although *T. aquaticus* DNA polymerase is especially preferred for use in PCR and other recombinant DNA techniques, there remains a need for other thermostable polymerases.

Accordingly, there is a desire in the art to produce a purified, thermostable DNA polymerase that may be used to improve the PCR process described above and to improve the results obtained when using a thermostable DNA polymerase in other recombinant techniques such as DNA sequencing, nick-translation, and even reverse transcription. The present invention helps meet that need by providing recombinant expression vectors and purification protocols for *Thermus thermophilus* DNA polymerase.

SUMMARY OF THE INVENTION

Accordingly, the present invention provides a purified thermostable enzyme that catalyzes combination of nucleoside triphosphates to form a nucleic acid strand complementary to a nucleic acid template strand. The purified enzyme is the DNA polymerase from *Thermus thermophilus* (Tth) and has a molecular weight predicted from the nucleic acid sequence of the gene of about 94 kDa. This purified material may be used in a temperature-cycling amplification reaction wherein nucleic acid sequences are produced from a given nucleic acid sequence in amounts that are large compared to the amount initially present so that the sequences can be manipulated and/or analyzed easily.

The gene encoding Tth DNA polymerase enzyme from *Thermus thermophilus* has also been identified and cloned and provides yet another means to prepare the thermostable enzyme of the present invention. In addition to the gene encoding the Tth enzyme, gene derivatives encoding Tth DNA polymerase activity are also provided.

The invention also encompasses a stable enzyme composition comprising a purified, thermostable Tth enzyme as described above in a buffer containing one or more non-ionic polymeric detergents.

Finally, the invention provides a method of purification for the thermostable polymerase of the invention. This method involves preparing a crude extract from *Thermus thermophilus* cells, adjusting the ionic strength of the crude extract so that the DNA polymerase dissociates from nucleic acid in the extract, subjecting the extract to hydrophobic interaction chromatography, subjecting the extract to DNA binding protein affinity chromatography, and subjecting the extract to cation or anion exchange or hydroxyapatite chromatography. In a preferred embodiment, these steps are carried out sequentially in the order given above, and non-ionic detergent is added to the extract prior to the DNA binding protein affinity chromatography step. The nucleotide binding protein affinity chromatography step is preferred for separating the DNA polymerase from endonuclease proteins.

DETAILED DESCRIPTION OF THE INVENTION

The present invention provides DNA sequences and expression vectors that encode Tth DNA polymerase. To facilitate understanding of the invention, a number of terms are defined below.

The terms "cell," "cell line," and "cell culture" can be used interchangeably and all such designations include progeny. Thus, the words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, and possibly other sequences. Eucaryotic cells are known to utilize promoters, polyadenylation signals, and enhancers.

The term "expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may also be integrated into the host chromosome.

The term "gene" refers to a DNA sequence that encodes a recoverable bioactive polypeptide or precursor. The polypeptide can be encoded by a full-length gene sequence or by any portion of the coding sequence so long as the enzymatic activity is retained.

The term "operably linked" refers to the positioning of the coding sequence such that control sequences will function to drive expression of the protein encoded by the coding sequence. Thus, a coding sequence "operably linked" to control sequences refers to a configuration wherein the coding sequences can be expressed under the control of a control sequence.

The term "mixture" as it relates to mixtures containing Tth polymerase refers to a collection of materials which includes Tth polymerase but which can also include other proteins. If the Tth polymerase is derived from recombinant host cells, the other proteins will ordinarily be those associated with the host. Where the host is bacterial, the contaminating proteins will, of course, be bacterial proteins.

The term "non-ionic polymeric detergents" refers to surface-active agents that have no ionic charge and that are characterized, for purposes of this invention, by an ability to stabilize the Tth enzyme at a pH range of from about 3.5 to about 9.5, preferably from 4 to 8.5.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be derived synthetically or by cloning.

The term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is initiated, i.e., in the presence of four different nucleoside triphosphates and the Tth thermostable enzyme in an appropriate buffer ("buffer" includes pH, ionic strength, cofactors, etc.) and at a suitable temperature. For Tth polymerase, the buffer preferably contains 1 to 3 mM of a magnesium salt, preferably $MgCl_2$, 50–200 mM of each nucleotide, and 0.5 to 1 mM of each primer, along with 50 mM KCl, 10 mM Tris buffer, pH 8–8.4, and 100 mg/ml gelatin (although gelatin is not required and should be avoided in some applications, such as DNA sequencing).

The primer is single-stranded for maximum efficiency in amplification, but may alternatively be double-stranded. If double-stranded, the primer is first treated to separate its strands before being used to prepare extension products. The primer is usually an oligodeoxyribonucleotide. The primer must be sufficiently long to prime the synthesis of extension products in the presence of the polymerase enzyme. The exact length of a primer will depend on many factors, such as source of primer and result desired, and the reaction temperature must be adjusted depending on primer length to ensure proper annealing of primer to template. Depending on the complexity of the target sequence, the oligonucleotide primer typically contains 15 to 35 nucleotides. Short primer molecules generally require cooler temperatures to form sufficiently stable complexes with template.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The terms "restriction endonucleases" and "restriction enzymes" refer to bacterial enzymes which cut double-stranded DNA at or near a specific nucleotide sequence.

The term "thermostable enzyme" refers to an enzyme which is stable to heat and is heat resistant and catalyzes (facilitates) combination of the nucleotides in the proper manner to form primer extension products that are complementary to each nucleic acid strand. Generally, synthesis of a primer extension product begins at the 3' end of the primer and proceeds in the 5' direction along the template strand, until synthesis terminates.

The Tth thermostable enzyme of the present invention satisfies the requirements for effective use in the amplification reaction known as the polymerase chain reaction. The Tth enzyme does not become irreversibly denatured (inactivated) when subjected to the elevated temperatures for the time necessary to effect denaturation of double-stranded nucleic acids, a key step in the PCR process. Irreversible denaturation for purposes herein refers to permanent and complete loss of enzymatic activity. The heating conditions necessary for nucleic acid denaturation will depend, e.g., on the buffer salt concentration and the composition and length of the nucleic acids being denatured, but typically range from about 90° to about 105° C. for a time depending mainly on the temperature and the nucleic acid length, typically from a few seconds up to four minutes. Higher temperatures may be tolerated as the buffer salt concentration and/or GC composition of the nucleic acid is increased. The Tth enzyme does not become irreversibly denatured for relatively short exposures to temperatures of about 90°–100° C.

The Tth thermostable enzyme has an optimum temperature at which it functions that is higher than about 50° C. Temperatures below 50° C. facilitate hybridization of primer to template, but depending on salt composition and concentration and primer composition and length, hybridization of primer to template can occur at higher temperatures (e.g., 45°–70° C.), which may promote specificity of the primer elongation reaction. The higher the temperature optimum for the enzyme, the greater the specificity and/or selectivity of the primer-directed extension process. The optimum temperature for Tth activity ranges from about 50° to 90° C.

The present invention provides the DNA sequence encoding a full-length thermostable DNA polymerase of *Thermus thermophilus*. This DNA sequence, Seq. ID No.30, and the deduced amino acid sequence, Seq. ID No.3, are depicted below. For convenience, the amino acid sequence of this Tth polymerase is numbered for reference, and other forms of the thermostable enzyme are designated by referring to changes from the full length, native sequence.

```
                                                                                           -61
            CCGAGGAGACCTACACCCCGGAGGGCGTGCGCTTCGCCCTCCTCCTCCCCAAGCCCGAGC

-1
            GGGAAGGTTTCCTCAGGGCGCTCCTGGACGCCACCCGGGGACAGGTGGCCCTGGAGTAGC 1                                                                               60
            ATGGAGGCGATGCTTCCGCTCTTTGAACCCAAAGGCCGGGTCCTCCTGGTGGACGGCCAC
            Met Glu Ala Met Leu Pro Leu Phe Glu Pro Lys Gly Arg Val Leu Leu Val Asp Gly His
            1                                                                               20

120
            CACCTGGCCTACCGCACCTTCTTCGCCCTGAAGGGCCTCACCACGAGCCGGGGCGAACCG
            His Leu Ala Tyr Arg Thr Phe Phe Ala Leu Lys Gly Leu Thr Thr Ser Arg Gly Glu Pro
                                                                                            40

180
            GTGCAGGCGGTCTACGGCTTCGCCAAGAGCCTCCTCAAGGCCCTGAAGGAGGACGGGTAC
            Val Gln Ala Val Tyr Gly Phe Ala Lys Ser Leu Leu Lys Ala Leu Lys Glu Asp Gly Tyr
                                                                                            60

240
            AAGGCCGTCTTCGTGGTCTTTGACGCCAAGGCCCCCTCCTTCCGCCACGAGGCCTACGAG
            Lys Ala Val Phe Val Val Phe Asp Ala Lys Ala Pro Ser Phe Arg His Glu Ala Tyr Glu
                                                                                            80

300
            GCCTACAAGGCGGGGAGGGCCCCGACCCCCGAGGACTTCCCCCGGCAGCTCGCCCTCATC
            Ala Tyr Lys Ala Gly Arg Ala Pro Thr Pro Glu Asp Phe Pro Arg Gln Leu Ala Leu Ile
                                                                                           100

360
            AAGGAGCTGGTGGACCTCCTGGGGTTTACCCGCCTCGAGGTCCCCGGCTACGAGGCGGAC
            Lys Glu Leu Val Asp Leu Leu Gly Phe Thr Arg Leu Glu Val Pro Gly Tyr Glu Ala Asp
                                                                                           120

420
            GACGTTCTCGCCACCCTGGCCAAGAAGGCGGAAAAGGAGGGGTACGAGGTGCGCATCCTC
            Asp Val Leu Ala Thr Leu Ala Lys Lys Ala Glu Lys Glu Gly Tyr Glu Val Arg Ile Leu
                                                                                           140

480
            ACCGCCGACCGCGACCTCTACCAACTCGTCTCCGACCGCGTCGCCGTCCTCCACCCCGAG
            Thr Ala Asp Arg Asp Leu Tyr Gln Leu Val Ser Asp Arg Val Ala Val Leu His Pro Glu
                                                                                           160

540
            GGCCACCTCATCACCCCGGAGTGGCTTTGGGAGAAGTACGGCCTCAGGCCGGAGCAGTGG
            Gly His Leu Ile Thr Pro Glu Trp Leu Trp Glu Lys Tyr Gly Leu Arg Pro Glu Gln Trp
                                                                                           180

600
            GTGGACTTCCGCGCCCTCGTGGGGGACCCCTCCGACAACCTCCCCGGGGTCAAGGGCATC
            Val Asp Phe Arg Ala Leu Val Gly Asp Pro Ser Asp Asn Leu Pro Gly Val Lys Gly Ile
                                                                                           200

660
            GGGGAGAAGACCGCCCTCAAGCTCCTCAAGGAGTGGGGAAGCCTGGAAAACCTCCTCAAG
            Gly Glu Lys Thr Ala Leu Lys Leu Leu Lys Glu Trp Gly Ser Leu Glu Asn Leu Leu Lys
                                                                                           220

720
            AACCTGGACCGGGTAAAGCCAGAAAACGTCCGGGAGAAGATCAAGGCCCACCTGGAAGAC
            Asn Leu Asp Arg Val Lys Pro Glu Asn Val Arg Glu Lys Ile Lys Ala His Leu Glu Asp
                                                                                           240
```

-continued

```
                                                                          780
CTCAGGCTCTCCTTGGAGCTCTCCCGGGTGCGCACCGACCTCCCCCTGGAGGTGGACCTC
Leu Arg Leu Ser Leu Glu Leu Ser Arg Val Arg Thr Asp Leu Pro Leu Glu Val Asp Leu
                                                                         260

840
GCCCAGGGGCGGGAGCCCGACCGGGAGGGGCTTAGGGCCTTCCTGGAGAGGCTGGAGTTC
Ala Gln Gly Arg Glu Pro Asp Arg Glu Gly Leu Arg Ala Phe Leu Glu Arg Leu Glu Phe
                                                                             280

900
GGCAGCCTCCTCCACGAGTTCGGCCTCCTGGAGGCGCCCGCCCCCCTGGAGGAGGCCCCC
Gly Ser Leu Leu His Glu Phe Gly Leu Leu Glu Ala Pro Ala Pro Leu Glu Glu Ala Pro
                                                                             300

960
TGGCCCCCGCCGGAAGGGGCCTTCGTGGGCTTCGTCCTCTCCCGCCCCGAGCCCATGTGG
Trp Pro Pro Glu Gly Ala Phe Val Gly Phe Val Leu Ser Arg Pro Glu Pro Met Trp
                                                                         320

1020
GCGGAGCTTAAAGCCCTGGCCGCCTGCAGGGACGGCCGGGTGCACCGGGCAGCAGACCCC
Ala Glu Leu Lys Ala Leu Ala Ala Cys Arg Asp Gly Arg Val His Arg Ala Ala Asp Pro
                                                                             340

1080
TTGGCGGGGCTAAAGGACCTCAAGGAGGTCCGGGGCCTCCTCGCCAAGGACCTCGCCGTC
Leu Ala Gly Leu Lys Asp Leu Lys Glu Val Arg Gly Leu Leu Ala Lys Asp Leu Ala Val
                                                                             360

1140
TTGGCCTCGAGGGAGGGGCTAGACCTCGTGCCCGGGGACGACCCCATGCTCCTCGCCTAC
Leu Ala Ser Arg Glu Gly Leu Asp Leu Val Pro Gly Asp Asp Pro Met Leu Leu Ala Tyr
                                                                             380

1200
CTCCTGGACCCCTCCAACACCACCCCCGAGGGGGTGGCGCGGCGCTACGGGGGGGAGTGG
Leu Leu Asp Pro Ser Asn Thr Thr Pro Glu Gly Val Ala Arg Arg Tyr Gly Gly Glu Trp
                                                                             400

1260
ACGGAGGACGCCGCCCACCGGGCCCTCCTCTCGGAGAGGCTCCATCGGAACCTCCTTAAG
Thr Glu Asp Ala Ala His Arg Ala Leu Leu Ser Glu Arg Leu His Arg Asn Leu Leu Lys
                                                                             420

1320
CGCCTCGAGGGGGAGGAGAAGCTCCTTTGGCTCTACCACGAGGTGGAAAAGCCCCTCTCC
Arg Leu Glu Gly Glu Glu Lys Leu Leu Trp Leu Tyr His Glu Val Glu Lys Pro Leu Ser
                                                                             440

1380
CGGGTCCTGGCCCACATGGAGGCCACCGGGGTACGGCTGGACGTGGCCTACCTTCAGGCC
Arg Val Leu Ala His Met Glu Ala Thr Gly Val Arg Leu Asp Val Ala Tyr Leu Gln Ala
                                                                             460

1440
CTTTCCCTGGAGCTTGCGGAGGAGATCCGCCGCCTCGAGGAGGAGGTCTTCCGCTTGGCG
Leu Ser Leu Glu Leu Ala Glu Glu Ile Arg Arg Leu Glu Glu Glu Val Phe Arg Leu Ala
                                                                             480

1500
GGCCACCCCTTCAACCTCAACTCCCGGGACCAGCTGGAAAGGGTGCTCTTTGACGAGCTT
Gly His Pro Phe Asn Leu Asn Ser Arg Asp Gln Leu Glu Arg Val Leu Phe Asp Glu Leu
                                                                             500

1560
AGGCTTCCCGCCTTGGGGAAGACGCAAAAGACAGGCAAGCGCTCCACCAGCGCCGCGGTG
Arg Leu Pro Ala Leu Gly Lys Thr Gln Lys Thr Gly Lys Arg Ser Thr Ser Ala Ala Val
                                                                             520

1620
CTGGAGGCCCTACGGGAGGCCCACCCCATCGTGGAGAAGATCCTCCAGCACCGGGAGCTC
Leu Glu Ala Leu Arg Glu Ala His Pro Ile Val Glu Lys Ile Leu Glu His Arg Glu Leu
                                                                             540

1680
ACCAAGCTCAAGAACACCTACGTGGACCCCCTCCCAAGCCTCGTCCACCCGAGGACGGGC
Thr Lys Leu Lys Asn Thr Tyr Val Asp Pro Leu Pro Ser Leu Val His Pro Arg Thr Gly
                                                                             560
```

-continued

```
                                                                        1740
CGCCTCCACACCCGCTTCAACCAGACGGCCACGGCCACGGGGAGGCTTAGTAGCTCCGAC
Arg Leu His Thr Arg Phe Asn Gln Thr Ala Thr Ala Thr Gly Arg Leu Ser Ser Ser Asp
                                                                         580

1800
CCCAACCTGCAGAACATCCCCGTCCGCACCCCCTTGGGCCAGAGGATCCGCCGGGCCTTC
Pro Asn Leu Gln Asn Ile Pro Val Arg Thr Pro Leu Gly Gln Arg Ile Arg Arg Ala Phe
                                                                         600

1860
GTGGCCGAGGCGGGTTGGGCGTTGGTGGCCCTGGACTATAGCCAGATAGAGCTCCGCGTC
Val Ala Glu Ala Gly Trp Ala Leu Val Ala Leu Asp Tyr Ser Gln Ile Glu Leu Arg Val
                                                                         620

1920
CTCGCCCACCTCTCCGGGGACGAAAACCTGATCAGGGTCTTCCAGGAGGGGAAGGACATC
Leu Ala His Leu Ser Gly Asp Glu Asn Leu Ile Arg Val Phe Gln Glu Gly Lys Asp Ile
                                                                         640

1980
CACACCCAGACCGCAAGCTGGATGTTCGGCGTCCCCCCGGAGGCCGTGGACCCCCTGATG
His Thr Gln Thr Ala Ser Trp Met Phe Gly Val Pro Pro Glu Ala Val Asp Pro Leu Met
                                                                         660

2040
CGCCGGGCGGCCAAGACGGTGAACTTCGGCGTCCTCTACGGCATGTCCGCCCATAGGCTC
Arg Arg Ala Ala Lys Thr Val Asn Phe Gly Val Leu Tyr Gly Met Ser Ala His Arg Leu
                                                                         680

2100
TCCCAGGAGCTTGCCATCCCCTACGAGGAGGCGGTGGCCTTTATAGAGCGCTACTTCCAA
Ser Gln Glu Leu Ala Ile Pro Tyr Glu Glu Ala Val Ala Phe Ile Glu Arg Tyr Phe Gln
                                                                         700

2160
AGCTTCCCCAAGGTGCGGGCCTGGATAGAAAAGACCCTGGAGGAGGGGAGGAAGCGGGGC
Ser Phe Pro Lys Val Arg Ala Trp Ile Glu Lys Thr Leu Glu Glu Gly Arg Lys Arg Gly
                                                                         720

2220
TACGTGGAAACCCTCTTCGGAAGAAGGCGCTACGTGCCCGACCTCAACGCCCGGGTGAAG
Tyr Val Glu Thr Leu Phe Gly Arg Arg Arg Tyr Val Pro Asp Leu Asn Ala Arg Val Lys
                                                                         740

2280
AGCGTCAGGGAGGCCGCGGAGCGCATGGCCTTCAACATGCCCGTCCAGGGCACCGCCGCC
Ser Val Arg Glu Ala Ala Glu Arg Met Ala Phe Asn Met Pro Val Gln Gly Thr Ala Ala
                                                                         760

2340
GACCTCATGAAGCTCGCCATGGTGAAGCTCTTCCCCCGCCTCCGGGAGATGGGGGCCCGC
Asp Leu Met Lys Leu Ala Met Val Lys Leu Phe Pro Arg Leu Arg Glu Met Gly Ala Arg
                                                                         780

2400
ATGCTCCTCCAGGTCCACGACGAGCTCCTCCTGGAGGCCCCCCAAGCGCGGGCCGAGGAG
Met Leu Leu Gln Val His Asp Glu Leu Leu Leu Glu Ala Pro Gln Ala Arg Ala Glu Glu
                                                                         800

2460
GTGGCGGCTTTGGCCAAGGAGGCCATGGAGAAGGCCTATCCCCTCGCCGTGCCCCTGGAG
Val Ala Ala Leu Ala Lys Glu Ala Met Glu Lys Ala Tyr Pro Leu Ala Val Pro Leu Glu
                                                                         820

2520
GTGGAGGTGGGGATGGGGGAGGACTGGCTTTCCGCCAAGGGTTAGGGGGGCCCTGCCGTT
Val Glu Val Gly Met Gly Glu Asp Trp Leu Ser Ala Lys Gly
                                                                         834
```

The DNA and amino acid sequences shown above and the DNA compounds that encode those sequences can be used to design and construct recombinant DNA expression vectors to drive expression of Tth DNA polymerase activity in a wide variety of host cells. A DNA compound encoding all or part of the DNA sequence shown above can also be used as a probe to identify thermostable polymerase-encoding DNA from other organisms, and the amino acid sequence shown above can be used to design peptides for use as immunogens to prepare antibodies that can be used to identify and purify a thermostable polymerase.

Whether produced by recombinant vectors that encode the above amino acid sequence or by native *Thermus thermophilus* cells, however, Tth DNA polymerase will typically be purified prior to use in a recombinant DNA technique. The present invention provides such purification methodology. For recovering the native protein the cells are grown using any suitable technique. Briefly, the cells are grown on a medium, in one liter, of nitrilotriacetic acid (100 mg), tryptone (3 g), yeast extract (3 g), succinic acid (5 g), sodium sulfite (50 mg), riboflavin (1 mg), $K_2HPO_4$ (522 mg), MgSO4 (480 mg), $CaCl_2$ (222 mg), NaCl (20 mg), and trace elements. The pH of the medium is adjusted to 8.0±0.2 with KOH. The yield is increased up to 20 g of cells/liter if cultivated with vigorous aeration at a temperature of 70° C. Cells in the late logarithmic growth stage (determined by absorbance at 550 nm) are collected by centrifugation, washed with a buffer and stored frozen at −20° C.

In another method for growing the cells, a defined mineral salts medium containing 0.3% glutamic acid supplemented with 0.1 mg/l biotin, 0.1 mg/l thiamine, and 0.05 mg/l nicotinic acid is employed. The salts include nitrilotriacetic acid, $CaSO_4$, $MgSO_4$, $NaCl$, $KNO_3$, $NaNO_3$, $ZnSO_4$, $H_3BO_3$, $CuSO_4$, $NaMoO_4$, $CoCl_2$, $FeCl_3$, $MnSO_4$, and $Na_2HPO_4$. The pH of the medium is adjusted to 8.0 with NaOH. The cells are grown initially at 75° C. in a water bath shaker. On reaching a certain density, one liter of these cells is transferred to a 14-liter fermentor. Sterile air is bubbled through the cultures and the temperature maintained at 75° C. The cells are allowed to grow for eight hours before being collected by centrifugation.

After cell growth, the isolation and purification of the enzyme takes place in six stages, each of which is carried out at a temperature below room temperature, preferably about 4° C. In the first stage or step, the cells, if frozen, are thawed, disintegrated with an Aminco French pressure cell (18,000 psi), suspended in a buffer at about pH 7.5, and centrifuged. In the second stage, the supernatant is collected and then fractionated by adding a salt such as dry ammonium sulfate. The pellet formed (at 0.2M $NH_4SO_4$) is discarded.

The supernatant from the second stage is applied to a phenyl sepharose column equilibrated with a buffer composed of 0.2M $(NH_4)_2SO_4$ 50 mM Tris-HCl, pH 7.5, and 0.5 mM DTT. Then the column is washed first with TE buffers and finally with a buffer containing 20% ethylene glycol. The protein is eluted in a buffer containing 2M urea.

In the fourth step, the eluate collected in the third step is applied to a heparin sepharose column equilibrated with 0.15M KCl. The column is then washed in the same buffer and the enzyme eluted with a linear gradient of a buffer such as 0.15M to 0.75 KCl. The activity peak is at 0.31 to 0.355M KCl.

In the fifth stage, the fraction collected in the fourth step is concentrated and diafiltered against Affigel blue buffer. The precipitate formed is removed by centrifugation, and the supernatant is applied to an Affigel-blue column equilibrated with 0.1M KCl. The column is then washed with 0.1M KCl and the enzyme eluted with a linear gradient of a buffer such as 0.1 to 0.5M KCl. Fractions with thermostable enzyme activity are then tested for contaminating deoxyribonucleases (endo- and exonucleases) using any suitable procedure. For example, the endonuclease activity may be determined electrophoretically from the change in molecular weight of phage λ DNA or supercoiled plasmid DNA after incubation with an excess of DNA polymerase. Similarly, exonuclease activity may be determined electrophoretically from the change in molecular weight of DNA after treatment with a restriction enzyme that cleaves at several sites. The fractions determined to have no deoxyribonuclease activity (peak activity of polymerase elutes at 0.28 to 0.455M KCl) are pooled and dialyzed against CM-Trisacryl buffer. The precipitate formed is removed by centrifugation.

In the sixth step, the supernatant is applied to a CM-Trisacryl column equilibrated with 50 mM NaCl. The column is washed with 50 mM NaCl and the enzyme eluted with a linear gradient of a buffer such as 0.05 to 0.4M NaCl. The pooled fractions having thermostable polymerase activity and no deoxyribonuclease activity elute at 0.16 to 0.20M NaCl.

The molecular weight of the dialyzed product may be determined by any technique, for example, by SDS-PAGE analysis using protein molecular weight markers. The molecular weight of the DNA polymerase purified from *Thermus thermophilus* is determined by the above method to be about 94 kDa. The molecular weight of this same DNA polymerase as determined by the predicted amino acid sequence is calculated to be approximately 94,016 daltons. The purification protocol of native Tth DNA polymerase is described in detail in Example 1. Purification of the recombinant Tth polymerase of the invention can be carried out with similar methodology.

An important aspect of the present invention is the production of recombinant Tth DNA polymerase. As noted above, the gene encoding this enzyme has been cloned from *Thermus thermophilus* genomic DNA. The complete coding sequence (~2.5 kb) for the Tth polymerase can be easily obtained in an ~3.7 kilobase (kb) HindIII-BstEII restriction fragment of plasmid pBSM:Tth10, although this ~3.7 kb fragment contains an internal HindIII restriction enzyme recognition site. This plasmid was deposited with the American Type Culture Collection (ATCC) in host cell *E. coli* K12 strain DG101 on Dec. 21, 1989, under accession No. 68195.

The complete coding sequence and deduced amino acid sequence of the thermostable Tth DNA polymerase enzyme is provided above. The entire coding sequence of the Tth DNA polymerase gene is not required, however, to produce a biologically active gene product with DNA polymerase activity. The availability of DNA encoding the Tth DNA polymerase sequence provides the opportunity to modify the coding sequence so as to generate mutein (mutant protein) forms also having DNA polymerase activity. Amino(N)-terminal deletions in the protein created by deletion of approximately one-third of the coding sequence result in the production of a gene product that is quite active in polymerase assays. Because certain N-terminal shortened forms of the polymerase are active, the gene constructs used for expression of these polymerases can include the corresponding shortened forms of the coding sequence. In addition to the N-terminal deletions, individual amino acid residues in the peptide chain comprising Tth polymerase may be modified by oxidation, reduction, or other derivation, and the protein may be cleaved to obtain fragments that retain activity. Such alterations that do not destroy activity do not remove the protein from the definition of a protein with Tth polymerase activity and so are specifically included within the scope of the present invention. Modifications to the primary structure of the Tth gene DNA polymerase by deletion, addition, or alteration so as to change the amino acids incorporated into the Tth DNA polymerase during translation can be made without destroying the high temperature DNA polymerase activity of the protein. Such substitutions or other alternations result in the production of proteins having an amino acid sequence encoded by DNA falling within the contemplated scope of the present invention. Likewise, the cloned genomic sequence, or homologous synthetic sequences, of the Tth DNA polymerase gene can be used to express a fusion polypeptide with Tth DNA polymerase activity or to express a protein with an amino acid sequence identical to that of native Tth DNA polymerase. In addition, such expression can be directed by the Tth DNA polymerase gene control sequences or by a control sequence that functions in whatever host is chosen to express the Tth DNA polymerase.

Thus, the present invention provides the complete coding sequence for Tth DNA polymerase from which expression vectors applicable to a variety of host systems can be constructed and the coding sequence expressed. Portions of the Tth polymerase-encoding sequence are also useful as probes to retrieve other thermostable polymerase-encoding sequences in a variety of species. Accordingly, portions of the genomic DNA encoding at least four to six amino acids can be replicated in *E. coli* and the denatured forms used as probes or oligodeoxyribonucleotide probes that encode at least four to six amino acids can be synthesized and used to retrieve additional DNAs encoding a thermostable polymerase. Because there may not be an exact match between the nucleotide sequence of the thermostable DNA polymerase gene of *Thermus thermophilus* and the corresponding gene of other species, oligomers containing approximately 12–18 nucleotides (encoding the four to six amino acid sequence) are usually necessary to obtain hybridization under conditions of sufficient stringency to eliminate false positives. Sequences encoding six amino acids supply ample information for such probes.

The present invention, by providing the coding and amino acid sequences for Tth DNA polymerase, therefore enables the isolation of other thermostable polymerase enzymes and the coding sequences for those enzymes. The Taq and Tth DNA polymerase coding sequences are very similar, and this similarity facilitated the identification and isolation of the Tth DNA polymerase coding sequence. The regions of dissimilarity between the Taq and Tth DNA polymerase coding sequences can also be used as probes, however, to identify other thermostable polymerase coding sequences that encode enzymes quite divergent from, for example, Taq polymerase but similar to Tth polymerase.

Several such regions of dissimilarity between the Taq and Tth DNA polymerase coding sequences exist. These regions include the sequences for codons 225–230; 238–246; 241–249; 335–343; 336–344; 337–345; 338–346; and 339–347. For regions nine codons in length, probes corresponding to these regions can be used to identify and isolate thermostable polymerase encoding DNA sequences that are identical (and complementary) to the probe for a contiguous sequence of at least five codons. For the region six codons in length, a probe corresponding to this region can be used to identify and isolate thermostable polymerase-encoding DNA sequences that are identical to the probe for a contiguous sequence of at least four codons. Such thermostable polymerase-encoding DNA sequences need not be from a *Thermus thermophilus* species, or even from the genus Thermus, to be isolated, so long as the requisite homology is present.

Whether one desires to produce an enzyme identical to native Tth DNA polymerase or a derivative or homologue of that enzyme, the production of a recombinant form of Tth polymerase typically involves the construction of an expression vector, the transformation of a host cell with the vector, and culture of the transformed host cell under conditions such that expression will occur. To construct the expression vector, a DNA is obtained that encodes the mature (used here to include all muteins) enzyme or a fusion of the Tth polymerase to an additional sequence that does not destroy activity or to an additional sequence cleavable under controlled conditions (such as treatment with peptidase) to give an active protein. The coding sequence is then placed in operable linkage with suitable control sequences in an expression vector. The vector can be designed to replicate autonomously in the host cell or to integrate into the chromosomal DNA of the host cell. The vector is used to transform a suitable host, and the transformed host is cultured under conditions suitable for expression of recombinant Tth polymerase. The Tth polymerase is isolated from the medium or from the cells; recovery and purification of the protein may not be necessary in some instances, where some impurities may be tolerated.

Each of the foregoing steps can be done in a variety of ways. For example the desired coding sequence may be obtained from genomic fragments and used directly in appropriate hosts. The construction for expression vectors operable in a variety of hosts are made using appropriate replicons and control sequences, as set forth generally below. Construction of suitable vectors containing the desired coding and control sequences employs standard ligation and restriction techniques that are well understood in the art. Isolated plasmids, DNA sequences, or synthesized oligonucleotides are cleaved, modified, and religated in the form desired. Suitable restriction sites can, if not normally available, be added to the ends of the coding sequence so as to facilitate construction of an expression vector, as exemplified below.

Site-specific DNA cleavage is performed by treating with the suitable restriction enzyme (or enzymes) under conditions that are generally understood in the art and specified by the manufacturers of commercially available restriction enzymes. See, e.g., New England Biolabs, Product Catalog. In general, about 1 µg of plasmid or other DNA is cleaved by one unit of enzyme in about 20 µl of buffer solution; in the examples below, an excess of restriction enzyme is generally used to ensure complete digestion of the DNA. Incubation times of about one to two hours at about 37° C. are typical, although variations can be tolerated. After each incubation, protein is removed by extraction with phenol and chloroform; this extraction can be followed by ether extraction and recovery of the DNA from aqueous fractions by precipitation with ethanol. If desired, size separation of the cleaved fragments may be performed by polyacrylamide gel or agarose gel electrophoresis using standard techniques. See, e.g., *Methods in Enzymology*, 1980, 65:499–560.

Restriction-cleaved fragments with single-strand "overhanging" termini can be made blunt-ended (double-strand ends) by treating with the large fragment of *E. coli* DNA polymerase I (Klenow) in the presence of the four deoxynucleoside triphosphates (dNTPs) using incubation times of about 15 to 25 minutes at 20° to 25° C. in 50 mM Tris pH 7.6, 50 mM NaCl, 10 mM $MgCl_2$, 10 mM DTT and 5 to 10 µM dNTPs. The Klenow fragment fills in at 5' protruding ends, but chews back protruding 3' single strands, even though the four dNTPs are present. If desired, selective repair can be performed by supplying only one of the, or selected, dNTPs within the limitations dictated by the nature of the protruding ends. After treatment with Klenow, the mixture is extracted with phenol/chloroform and ethanol precipitated. Similar results can be achieved using S 1 nuclease, because treatment under appropriate conditions with S 1 nuclease results in hydrolysis of any single-stranded portion of a nucleic acid.

Synthetic oligonucleotides can be prepared using the triester method of Matteucci et al., 1981, *J. Am. Chem. Soc.* 103:3185–3191 or automated synthesis methods. Kinasing of single strands prior to annealing or for labeling is achieved using an excess, e.g., approximately 10 units, of polynucleotide kinase to 0.5 µM substrate in the presence of 50 mM Tris, pH 7.6, 10 mM $MgCl_2$, 5 mM dithiothreitol (DTT), and 1 to 2 µM ATP. If kinasing is for labeling of probe, the ATP will contain high specific activity $\gamma$-$^{32}$P.

Ligations are performed in 15–30 µl volumes under the following standard conditions and temperatures: 20 mM Tris-Cl, pH 7.5, 10 mM $MgCl_2$, 10 mM DTT, 33 µg/ml BSA, 10 mM-50 mM NaCl, and either 40 μM ATP and 0.01-0.02 (Weiss) units T4 DNA ligase at 0° C. (for ligation of fragments with complementary single-stranded ends) or 1 mM ATP and 0.3-0.6 units T4 DNA ligase at 14° C. (for "blunt end" ligation). Intermolecular ligations of fragments with complementary ends are usually performed at 33-100 μg/ml total DNA concentrations (5-100 nM total ends concentration). Intermolecular blunt end ligations (usually employing a 10-30 fold molar excess of linkers) are performed at 1 μM total ends concentration.

In vector construction, the vector fragment is commonly treated with bacterial or calf intestinal alkaline phosphatase (BAP or CIAP) to remove the 5' phosphate and prevent religation and reconstruction of the vector. BAP and CIAP digestion conditions are well known in the art, and published protocols usually accompany the commercially available BAP and CIAP enzymes. To recover the nucleic acid fragments, the preparation is extracted with phenol-chloroform and ethanol precipitated to remove AP and purify the DNA. Alternatively, religation can be prevented by restriction enzyme digestion of unwanted vector fragments before or after ligation of the desired vector.

For portions of vectors or coding sequences that require sequence modifications, a variety site-specific primer-directed mutagenesis methods are available. The polymerase chain reaction (PCR) can be used to perform site-specific mutagenesis. In another technique now standard in the art, a synthetic oligonucleotide encoding the desired mutation is used as a primer to direct synthesis of a complementary nucleic acid sequence of a single-stranded vector, such pBS13+, that serves as a template for construction of the extension product of the mutagenizing primer. The mutagenized DNA is transformed into a host bacterium, and cultures of the transformed bacteria are plated and identified. The identification of modified vectors may involve transfer of the DNA of selected transformants to a nitrocellulose filter or other membrane and the "lifts" hybridized with kinased synthetic primer at a temperature that permits hybridization of an exact match to the modified sequence but prevents hybridization with the original strand. Transformants that contain DNA that hybridizes with the probe are then cultured and serve as a reservoir of the modified DNA.

In the constructions set forth below, correct ligations for plasmid construction are confirmed by first transforming *E. coli* strain DG101 or another suitable host, with the ligation mixture. Successful transformants are selected by ampicillin, tetracycline or other antibiotic resistance or sensitivity or by using other markers, depending on the mode of plasmid construction, as is understood in the art. Plasmids from the transformants are then prepared according to the method of Clewell et al., 1969, *Proc. Natl. Acad. Sci. USA* 62:1159, optionally following chloramphenicol amplification (Clewell, 1972, *J. Bacteriol.* 110:667). Another method for obtaining plasmid DNA is described as the "Base-Acid" extraction method at page 11 of the Bethesda Research Laboratories publication Focus, volume 5, number 2, and very pure plasmid DNA can be obtained by replacing steps 12 through 17 of the protocol with CsCl/ethidium bromide ultracentrifugation of the DNA. The isolated DNA is analyzed by restriction enzyme digestion and/or sequenced by the dideoxy method of Sanger et al., 1977, *Proc. Natl. Acad. Sci. USA* 74:5463, as further described by Messing et al., 1981, *Nuc. Acids Res.* 9:309, or by the method of Maxam et al., 1980, *Methods in Enzymology* 65:499.

The control sequences, expression vectors, and transformation methods are dependent on the type of host cell used to express the gene. Generally, procaryotic, yeast, insect, or mammalian cells are used as hosts. Procaryotic hosts are in general the most efficient and convenient for the production of recombinant proteins and are therefore preferred for the expression of Tth polymerase.

The procaryote most frequently used to express recombinant proteins is *E. coli*. For cloning and sequencing, and for expression of constructions under control of most bacterial promoters, *E. coli* K12 strain MM294, obtained from the *E. coli* Genetic Stock Center under GCSC #6135, can be used as the host. For expression vectors with the $P_L N_{RBS}$ control sequence, *E. coli* K12 strain MC1000 lambda lysogen, $N_7 N_{53} cI857 SusP_{80}$, ATCC 39531, may be used. *E. coli* DG116, which was deposited with the ATCC (ATCC 53606) on Apr. 7, 1987, and *E. coli* KB2, which was deposited with the ATCC (ATCC 53075) on Mar. 29, 1985, are also useful host cells. For M13 phage recombinants, *E. coli* strains susceptible to phage infection, such as *E. coli* K12 strain DG98, are employed. The DG98 strain was deposited with the ATCC (ATCC 39768) on Jul. 13, 1984.

However, microbial strains other than *E. coli* can also be used, such as bacilli, for example *Bacillus subtilis*, various species of Pseudomonas, and other bacterial strains, for recombinant expression of Tth DNA polymerase. In such procaryotic systems, plasmid vectors that contain replication sites and control sequences derived from the host or a species compatible with the host are typically used.

For example, *E. coli* is typically transformed using derivatives of pBR322, described by Bolivar et al., 1977, *Gene* 2:95. Plasmid pBR322 contains genes for ampicillin and tetracycline resistance. These drug resistance markers can be either retained or destroyed in constructing the desired vector and so help to detect the presence of a desired recombinant. Commonly used procaryotic control sequences, i.e., a promoter for transcription initiation, optionally with an operator, along with a ribosome binding site sequence, include the β- lactamase (penicillinase) and lactose (lac) promoter systems (Chang et al., 1977, *Nature* 198:1056), the tryptophan (trp) promoter system (Goeddel et al., 1980, *Nuc. Acids Res.* 8:4057), and the lambda-derived $P_L$ promoter (Shimatake et al., 1981, *Nature* 292:128) and N-gene ribosome binding site ($N_{RBS}$). A portable control system cassette is set forth in U.S. Pat. No. 4,711,845, issued Dec. 8, 1987. This cassette comprises a $P_L$ promoter operably linked to the $N_{RBS}$ in turn positioned upstream of a third DNA sequence having at least one restriction site that permits cleavage within six bp 3' of the $N_{RBS}$ sequence. Also useful is the phosphatase A (phoA) system described by Chang et al. in European Patent Publication No. 196,864, published Oct. 8, 1986. However, any available promoter system compatible with procaryotes can be used to construct a Tth expression vector of the invention.

In addition to bacteria, eucaryotic microbes, such as yeast, can also be used as recombinant host cells. Laboratory strains of *Saccharomyces cerevisiae*, Baker's yeast, are most often used, although a number of other strains are commonly available. While vectors employing the two micron origin of replication are common (Broach, 1983, *Meth. Enz.* 101:307), other plasmid vectors suitable for yeast expression are known (see, for example, Stinchcomb et al., 1979, *Nature* 282:39; Tschempe et al., 1980, *Gene* 10: 157; and Clarke et al., 1983, *Meth. Enz.* 101 :300). Control sequences for yeast vectors include promoters for the synthesis of glycolytic enzymes (Hess et al., 1968, *J. Adv. Enzyme Reg.* 7:149, and Holland et a., 1978, *Biotechnology* 17:4900). Additional promoters known in the art include the promoter for 3-phosphoglycerate kinase (Hitzeman et al., 1980, *J. Biol. Chem.* 255:2073) and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization (Holland, supra).

Terminator sequences may also be used to enhance expression when placed at the 3' end of the coding sequence. Such terminators are found in the 3' untranslated region following the coding sequences in yeast-derived genes. Many vectors contain control sequences derived from the enolase gene contained in plasmid peno46 (Holland et al., 1981, *J. Biol. Chem.* 256:1385) or the LEU2 gene obtained from YEp13 (Broach et al, 1978, *Gene* 8:121); however, any vector containing a yeast-compatible promoter, origin of replication, and other control sequences is suitable for use in constructing yeast Tth expression vectors.

The Tth gene can also be expressed in eucaryotic host cell cultures derived from multicellular organisms. See, for example, *Tissue Culture*, Academic Press, Cruz and Patterson, editors (1973). Useful host cell lines include COS-7, COS-A2, CV-1, murine cells such as murine myelomas N51 and VERO, HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers et al., 1978, *Nature* 273:113), or other viral promoters such as those derived from polyoma, adenovirus 2, bovine papilloma virus (BPV), or avian sarcoma viruses, or immunoglobulin promoters and heat shock promoters. A system for expressing DNA in mammalian systems using a BPV vector system is disclosed in U.S. Pat. No. 4,419,446. A modification of this system is described in U.S. Pat. No. 4,601,978. General aspects of mammalian cell host system transformations have been described by Axel, U.S. Pat. No. 4,399,216. "Enhancer" regions are also important in optimizing expression; these are, generally, sequences found upstream of the promoter region. Origins of replication may be obtained, if needed, from viral sources. However, integration into the chromosome is a common mechanism for DNA replication in eucaryotes.

Plant cells can also be used as hosts, and control sequences compatible with plant cells, such as the nopaline synthase promoter and polyadenylation signal sequences (Depicker et al., 1982, *J. Mol. Appl. Gen.* 1:561) are available. Expression systems employing insect cells utilizing the control systems provided by baculovirus vectors have also been described (Miller et al., in *Genetic Engineering* (1986) Setlow et al., eds., Plenum Publishing, Vol. 8, pp. 277-297). Insect cell-based expression can be accomplished in *Spodoptera frugipeida*. These systems are also successful in producing recombinant Tth polymerase.

Depending on the host cell used, transformation is done using standard techniques appropriate to such cells. The calcium treatment employing calcium chloride, as described by Cohen, 1972, *Proc. Natl. Acad. Si. USA* 69:21 10 is used for procaryotes or other cells that contain substantial cell wall barriers. Infection with *Agrobacterium tumefaciens* (Shaw et al., 1983, *Gene* 2:315) is used for certain plant cells. For mammalian cells, the calcium phosphate precipitation method of Graham and van der Eb, 1978, *Virology* 52:546 is preferred. Transformations into yeast are carried out according to the method of Van Solingen et al., 1977, *J. Bact.* 130:946 and Hsiao et al., 1979, *Proc. Natl. Acad. Sci. USA* 76:3829.

Once the Tth DNA polymerase has been expressed in a recombinant host cell, purification of the protein may be desired. Although the purification procedures previously described can be used to purify the recombinant thermostable polymerase of the invention, hydrophobic interaction chromatography purification methods are preferred. Hydrophobic interaction chromatography is a separation technique in which substances are separated on the basis of differing strengths of hydrophobic interaction with an uncharged bed material containing hydrophobic groups. Typically, the column is first equilibrated under conditions favorable to hydrophobic binding, e.g., high ionic strength. A descending salt gradient may be used to elute the sample.

According to the invention, the aqueous mixture (containing either native or recombinant Tth DNA polymerase) is loaded onto a column containing a relatively strong hydrophobic gel such as phenyl sepharose (manufactured by Pharmacia) or Phenyl TSK (manufactured by Toyo Soda). To promote hydrophobic interaction with a phenyl sepharose column, a solvent is used which contains, for example, greater than or equal to 0.2M ammonium sulfate, with 0.2M being preferred. The column and the sample are adjusted to 0.2M ammonium sulfate in 50 mM Tris, pH 7.5, and 1 mM EDTA ("TE") buffer that also contains 1 mM DTT and the sample applied to the column. The column is washed with the 0.2M ammonium sulfate buffer. The enzyme may then be eluted with solvents which attenuate hydrophobic interactions such as, for example, decreasing salt gradients, ethylene or propylene glycol, or urea. For recombinant Tth polymerase, a preferred embodiment involves washing the column sequentially with the Tris-EDTA buffer and the Tris-EDTA buffer containing 20% ethylene glycol. The Tth polymerase is subsequently eluted from the column with a 0 to 4M urea gradient in the Tris-EDTA ethylene glycol buffer.

For long-term stability, Tth DNA polymerase enzyme must be stored in a buffer that contains one or more non-ionic polymeric detergents. Such detergents are generally those that have a molecular weight in the range of approximately 100 to 250,000 preferably about 4,000 to 200,000 daltons and stabilize the enzyme at a pH of from about 3.5 to about 9.5, preferably from about 4 to 8.5. Examples of such detergents include those specified on pages 295-298 of McCutcheon's *Emulsifiers & Detergents*, North American edition (1983), published by the McCutcheon Division of MC Publishing Co., 175 Rock Road, Glen Rock, N.J. (USA), the entire disclosure of which is incorporated herein by reference. Preferably, the detergents are selected from the group comprising ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers. More particularly preferred are Tween 20, a polyoxyethylated (20) sorbitan monolaurate from ICI Americas Inc., Wilmington, Del., and Iconol™ NP-40, an ethoxylated alkyl phenol (nonyl) from BASF Wyandotte Corp. Parsippany, N.J.

The thermostable enzyme of this invention may be used for any purpose in which such enzyme activity is necessary or desired. In a particularly preferred embodiment, the enzyme catalyzes the nucleic acid amplification reaction known as PCR. This process for amplifying nucleic acid sequences is disclosed and claimed in U.S. Pat. No. 4,683,202, issued Jul. 28, 1987, the disclosure of which is incorporated herein by reference. The PCR nucleic acid amplification method involves amplifying at least one specific nucleic acid sequence contained in a nucleic acid or a mixture of nucleic acids and produces double-stranded DNA.

For ease of discussion, the protocol set forth below assumes that the specific sequence to be amplified is contained in a double-stranded nucleic acid. However, the process is equally useful in amplifying single-stranded nucleic acid, such as mRNA, although in the preferred embodiment the ultimate product is still double-stranded DNA. In the amplification of a single-stranded nucleic acid, the first step involves the synthesis of a complementary strand (one of the two amplification primers can be used for this purpose), and the succeeding steps proceed as in the double-stranded amplification process described below.

This amplification process comprises the steps of:

(a) contacting each nucleic acid strand with four different nucleoside triphosphates and one oligonucleotide primer for each strand of the specific sequence being amplified, wherein each primer is selected to be substantially complementary to the different strands of the specific sequence, such that the extension product synthesized from one primer, when it is separated from its complement, can serve as a template for synthesis of the extension product of the other primer, said contacting being at a temperature which allows hybridization of each primer to a complementary nucleic acid strand;

(b) contacting each nucleic acid strand; at the same time as or after step (a), with a DNA polymerase from *Thermus thermophilus* which enables combination of the nucleoside triphosphates to form primer extension products complementary to each strand of the specific nucleic acid sequence;

(c) maintaining the mixture from step (b) at an effective temperature for an effective time to promote the activity of the enzyme and to synthesize, for each different sequence being amplified, an extension product of each primer which is complementary to each nucleic acid strand template, but not so high as to separate each extension product from the complementary strand template;

(d) heating the mixture from step (c) for an effective time and at an effective temperature to separate the primer extension products from the templates on which they were synthesized to produce single-stranded molecules but not so high as to denature irreversibly the enzyme;

(e) cooling the mixture from step (d) for an effective time and to an effective temperature to promote hybridization of a primer to each of the single-stranded molecules produced in step (d); and (f) maintaining the mixture from step (e) at an effective temperature for an effective time to promote the activity of the enzyme and to synthesize, for each different sequence being amplified, an extension product of each primer which is complementary to each nucleic acid strand template produced in step (d) but not so high as to separate each extension product from the complementary strand template. The effective times and temperatures in steps (e) and (f) may coincide, so that steps (e) and (f) can be carried out simultaneously. Steps (d)–(f) are repeated until the desired level of amplification is obtained.

The amplification method is useful not only for producing large amounts of a specific nucleic acid sequence of known sequence but also for producing nucleic acid sequences which are known to exist but are not completely specified. One need know only a sufficient number of bases at both ends of the sequence in sufficient detail so that two oligonucleotide primers can be prepared which will hybridize to different strands of the desired sequence at relative positions along the sequence such that an extension product synthesized from one primer, when separated from the template (complement), can serve as a template for extension of the other primer into a nucleic acid sequence of defined length. The greater the knowledge about the bases at both ends of the sequence, the greater can be the specificity of the primers for the target nucleic acid sequence and the efficiency of the process. In any case, an initial copy of the sequence to be amplified must be available, although the sequence need not be pure or a discrete molecule. In general, the amplification process involves a chain reaction for producing, in exponential quantities relative to the number of reaction steps involved, at least one specific nucleic acid sequence given that (a) the ends of the required sequence are known in sufficient detail that oligonucleotides can be synthesized which will hybridize to them, and (b) that a small amount of the sequence is available to initiate the chain reaction. The product of the chain reaction will be a discrete nucleic acid duplex with termini corresponding to the ends of the specific primers employed.

Any nucleic acid sequence, in purified or nonpurified form, can be utilized as the starting nucleic acid(s), provided it contains or is suspected to contain the specific nucleic acid sequence desired. The nucleic acid to be amplified can be obtained from any source, for example, from plasmids such as pBR322, from cloned DNA or RNA, or from natural DNA or RNA from any source, including bacteria, yeast, viruses, organelles, and higher organisms such as plants and animals. DNA or RNA may be extracted from blood, tissue material such as chorionic villi, or amniotic cells by a variety of techniques. See, e.g., Maniatis et al., supra, pp. 280–281. Thus, the process may employ, for example, DNA or RNA, including messenger RNA, which DNA or RNA may be single-stranded or double-stranded. In addition, a DNA-RNA hybrid which contains one strand of each may be utilized. A mixture of any of these nucleic acids can also be employed as can nucleic acids produced from a previous amplification reaction (using the same or different primers). The specific nucleic acid sequence to be amplified may be only a fraction of a large molecule or can be present initially as a discrete molecule, so that the specific sequence constitutes the entire nucleic acid.

The sequence to be amplified need not be present initially in a pure form; the sequence can be a minor fraction of a complex mixture, such as a portion of the β- globin gene contained in whole human DNA (as exemplified in Saiki et al., 1985, *Science* 230:1530–1534) or a portion of a nucleic acid sequence due to a particular microorganism, which organism might constitute only a very minor fraction of a particular biological sample. The cells can be directly used in the amplification process after suspension in hypotonic buffer and heat treatment at about 90°–100° C. until cell lysis and dispersion of intracellular components occur (generally 1 to 15 minutes). After the heating step, the amplification reagents may be added directly to the lysed cells. The starting nucleic acid sequence may contain more than one desired specific nucleic acid sequence. The amplification process is useful not only for producing large amounts of one specific nucleic acid sequence but also for amplifying simultaneously more than one different specific nucleic acid sequence located on the same or different nucleic acid molecules.

Primers play a key role in the PCR process. The word "primer" as used in describing the amplification process can refer to more than one primer, particulary in the case where there is some ambiguity in the information regarding the terminal sequence(s) of the fragment to be amplified. For instance, in the case where a nucleic acid sequence is inferred from protein sequence information, a collection of primers containing sequences representing all possible codon variations based on degeneracy of the genetic code will be used for each strand. One primer from this collection will be sufficiently homologous with the end of the desired sequence to be amplified to be useful for amplification.

In addition, more than one specific nucleic acid sequence can be amplified from the first nucleic acid or mixture of nucleic acids, so long as the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process.

A sequence within a given sequence can be amplified after a given number of amplification cycles to obtain greater specificity of the reaction by adding after at least one cycle of amplification a set of primers that are complementary to internal sequences (that are not on the ends) of the sequence to be amplified. Such primers may be added at any stage and will provide a shorter amplified fragment. Alternatively, a longer fragment can be prepared by using primers with 5' ends but having some overlap with the primers previously utilized in the amplification.

Primers also play a key role when the amplification process is used for in vitro mutagenesis. The product of an amplification reaction where the primers employed are not exactly complementary to the original template will contain the sequence of the primer rather than the template, so introducing an in vitro mutation. In further cycles this mutation will be amplified with an undiminished efficiency because no further mispaired priming is required. The process of making an altered DNA sequence as described above could be repeated on the altered DNA using different primers to induce further sequence changes. In this way, a series of mutated sequences can gradually be produced wherein each new addition to the series differs from the last in a minor way, but from the original DNA source sequence in an increasingly major way.

Because the primer can contain as part of its sequence a non-complementary sequence, provided that a sufficient amount of the primer contains a sequence that is complementary to the strand to be amplified, many other advantages can be realized. For example, a nucleotide sequence that is not complementary to the template sequence (such as, e.g., a promoter, linker, coding sequence, etc.) may be attached at the 5' end of one or both of the primers and so appended to the product of the amplification process. After the extension primer is added, sufficient cycles are run to achieve the desired amount of new template containing the non-complementary nucleotide insert. This allows production of large quantities of the combined fragments in a relatively short period of time (e.g., two hours or less) using a simple technique.

Oligonucleotide primers can be prepared using any suitable method, such as, for example, the phosphotriester and phosphodiester methods described above, or automated embodiments thereof. In one such automated embodiment, diethylphosphoramidites are used as starting materials and may be synthesized as described by Beaucage et al., 1981, *Tetrahedron Letters* 22:1859–1862. One method for synthesizing oligonucleotides on a modified solid support is described in U.S. Pat. No. 4,458,066. One can also use a primer that has been isolated from a biological source (such as a restriction endonuclease digest).

No matter what primers are used, however, the reaction mixture must contain a template for PCR to occur, because the specific nucleic acid sequence is produced by using a nucleic acid containing that sequence as a template. The first step involves contacting each nucleic acid strand with four different nucleoside triphosphates and one oligonucleotide primer for each strand of each specific nucleic acid sequence being amplified or detected. If the nucleic acids to be amplified or detected are DNA, then the nucleoside triphosphates are usually dATP, dCTP, dGTP, and TTP, although various nucleotide derivatives can also be used in the process. The concentration of nucleotide triphosphates can vary widely. Typically the concentration is 50–200 µM in each dNTP in the buffer for amplification, and $MgCl_2$ is present in the buffer in an amount of 1 to 3 mM to increase the efficiency and specificity of the reaction. However, dNTP concentrations of 1–20 µM may be preferred for some applications, such as DNA sequencing.

The nucleic acids strands of the target nucleic acid serve as templates for the synthesis of additional nucleic acids strands, which are extension products of the primers. This synthesis can be performed using any suitable method, but generally occurs in a buffered aqueous solution, preferably at a pH of 7–9, most preferably about 8. To facilitate synthesis, a molar excess (for cloned nucleic acid, usually about 1000:1 primer:template and for genomic nucleic acid, usually about $10^8$:1 primer:template) of the two oligonucleotide primers is added to the buffer containing the template strands. As a practical matter, the amount of primer added will generally be in molar excess over the amount of complementary strand (template) when the sequence to be amplified is contained in a mixture of complicated long-chain nucleic acid strands. A large molar excess is preferred to improve the efficiency of the process.

The mixture of template, primers, and nucleoside triphosphates is then treated according to whether the nucleic acids being amplified or detected are double- or single-stranded. If the nucleic acids are single-stranded, then no denaturation step need be employed, and the reaction mixture is held at a temperature which promotes hybridization of the primer to its complementary target (template) sequence. Such temperature is generally from about 35° C. to 65° C. or more, preferably about 37°–60° C. for an effective time, generally from a few seconds to five minutes, preferably from 30 seconds to one minute. A hybridization temperature of 45°–58° C. is used for Tth DNA polymerase, and 15-mer or longer primers are used to increase the specificity of primer hybridization. Shorter primers require lower hybridization temperatures. The complement to the original single-stranded nucleic acids can be synthesized by adding Tth DNA polymerase in the presence of the appropriate buffer, dNTPs, and one or more oligonucleotide primers. If an appropriate single primer is added, the primer extension product will be complementary to the single-stranded nucleic acid and will be hybridized with the nucleic acid strand in a duplex of strands of equal or unequal length (depending on where the primer hybridizes to the template), which may then be separated into single strands as described above to produce two single, separated, complementary strands. Alternatively, two or more appropriate primers (one of which will prime synthesis using the extension product of the other primer as a template) may be added to the single-stranded nucleic acid and the reaction carried out If the nucleic acid contains two strands, as in the case of amplification of a double-stranded target or second-cycle amplification of a single-stranded target, the strands of nucleic acid must be separated before the primers are hybridized. This strand separation can be accomplished by any suitable denaturing method, including physical, chemical or enzymatic means. One preferred physical method of separating the strands of the nucleic acid involves heating the nucleic acid until complete (>99%) denaturation occurs. Typical heat denaturation involves temperatures ranging from about 90° to 105° C. for times generally ranging from about a few seconds to 5 minutes, depending on the composition and size of the nucleic acid. Preferably, the effective denaturing temperature is 90°–100° C. for 10 seconds to 3 minutes. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Kuhn Hoffmann-Berling, 1978, *CSH-Quantitative Biology* 43:63, and techniques for using RecA are reviewed in Radding, 1982, *Ann. Rev. Genetics* 16:405–437. The denaturation produces two separated complementary strands of equal or unequal length.

If the double-stranded nucleic acid is denatured by heat, the reaction mixture is allowed to cool to a temperature which promotes hybridization of each primer to the complementary target (template) sequence. This temperature is usually from about 35° C. to 65° C. or more, depending on reagents, preferably 37°–60° C. The hybridization temperature is maintained for an effective time, generally 30 seconds to 5 minutes, and preferably 1–3 minutes. In practical terms, the temperature is simply lowered from about 95° C. to as low as 37° C., and hybridization occurs at a temperature within this range.

Whether the nucleic acid is single- or double-stranded, the DNA polymerase from *Thermus thermophilus* may be added at the denaturation step or when the temperature is being reduced to or is in the range for promoting hybridization. Although the thermostability of Tth polymerase allows one to add Tth polymerase to the reaction mixture at any time, one can substantially inhibit non-specific amplification by adding the polymerase to the reaction mixture at a point in time when the mixture will not be cooled below the stringent hybridization temperature. After hybridization, the reaction mixture is then heated to or maintained at a temperature at which the activity of the enzyme is promoted or optimized, i.e., a temperature sufficient to increase the activity of the enzyme in facilitating synthesis of the primer extension products from the hybridized primer and template. The temperature must actually be sufficient to synthesize an extension product of each primer which is complementary to each nucleic acid template, but must not be so high as to denature each extension product from its complementary template (i.e., the temperature is generally less than about 80°–90° C.).

Depending on the nucleic acid(s) employed, the typical temperature effective for this synthesis reaction generally ranges from about 40° to 80° C., preferably 50°–75° C. The temperature more preferably ranges from about 65°–75° C. for *Thermus thermophilius* DNA polymerase. The period of time required for this synthesis may range from about 0.5 to 40 minutes or more, depending mainly on the temperature, the length of the nucleic acid, the enzyme, and the complexity of the nucleic acid mixture. The extension time is usually about 30 seconds to three minutes. If the nucleic acid is longer, a longer time period is generally required for complementary strand synthesis.

The newly synthesized strand and the complement nucleic acid strand form a double-stranded molecule which is used in the succeeding steps of the amplification process. In the next step, the strands of the double-stranded molecule are separated by heat denaturation at a temperature and for a time effective to denature the molecule, but not at a temperature and for a period so long that the thermostable enzyme is completely and irreversibly denatured or inactivated. After this denaturation of template, the temperature is decreased to a level which promotes hybridization of the primer to the complementary single-stranded molecule (template) produced from the previous step, as described above.

After this hybridization step, or concurrently with the hybridization step, the temperature is adjusted to a temperature that is effective to promote the activity of the thermostable enzyme to enable synthesis of a primer extension product using as a template both the newly synthesized and the original strands. The temperature again must not be so high as to separate (denature) the extension product from its template, as described above. Hybridization may occur during this step, so that the previous step of cooling after denaturation is not required. In such a case, using simultaneous steps, the preferred temperature range is 50°–70° C.

The heating and cooling steps involved in one cycle of strand separation, hybridization, and extension product synthesis can be repeated as often as needed to produce the desired quantity of the specific nucleic acid sequence. The only limitation is the amount of the primers, thermostable enzyme, and nucleotide triphosphates present. Usually, from 15 to 30 cycles are completed. For diagnostic detection of amplified DNA, the number of cycles will depend on the nature of the sample. For example, fewer cycles will be required if the sample being amplified is pure. If the sample is a complex mixture of nucleic acids, more cycles will be required to amplify the signal sufficiently for detection. For general amplification and detection, the process is repeated about 15 times. When amplification is used to generate sequences to be detected with labeled sequence-specific probes and when human genomic DNA is the target of amplification, the process is repeated 15 to 30 times to amplify the sequence sufficiently that a clearly detectable signal is produced, i.e., so that background noise does not interfere with detection.

No additional nucleotides, primers, or thermostable enzyme need be added after the initial addition, provided that no key reagent has been exhausted and that the enzyme has not become denatured or inactivated irreversibly, in which case additional polymerase or other reagent would have to be added for the reaction to continue. Addition of such materials at each step, however, will not adversely affect the reaction. After the appropriate number of cycles have been completed to produce the desired amount of the specific nucleic acid sequence, the reaction may be halted in the usual manner, e.g., by inactivating the enzyme by adding EDTA, phenol, SDS, or $CHCl_3$ or by separating the components of the reaction.

The amplification process may be conducted continuously. In one embodiment of an automated process, the reaction mixture may be temperature cycled such that the temperature is programmed to be controlled at a certain level for a certain time. One such instrument for this purpose is the automated machine for handling the amplification reaction developed and marketed by Perkin Elmer, Norwalk, Conn. Detailed instructions for carrying out PCR with the instrument are available upon purchase of the instrument.

Tth DNA polymerase is very useful in carrying out the diverse processes in which amplification of a nucleic acid sequence by the polymerase chain reaction is useful. The amplification method may be utilized to clone a particular nucleic acid sequence for insertion into a suitable expression vector, as described in U.S. Pat. No. 4,800,159. The vector may be used to transform an appropriate host organism to produce the gene product of the sequence by standard methods of recombinant DNA technology. Such cloning may involve direct ligation into a vector using blunt-end ligation, or use of restriction enzymes to cleave at sites contained within the primers. Other processes suitable for Tth polymerase include those described in U.S. Pat. Nos. 4,683,194; 4,683,195; and 4,683,202 and European Patent Publication Nos. 229,701; 237,362; and 258,017; these patents and publications are incorporated herein by reference. In addition, the present enzyme is useful in asymmetric PCR (see Gyllensten and Erlich, 1988, *Proc. Natl. Acad. Sci. USA* 85:7652–7656, incorporated herein by reference); inverse PCR (Ochman et al., 1988, *Genetics* 120:621, incorporated herein by reference); and for DNA sequencing (see Innis et al., 1988, *Proc. Natl. Acad. Sci. USA* 85:9436–9440, and McConlogue et al., 1988, *Nuc. Acids Res.* 16(20):9869). Tth polymerase also has reverse transcriptase activity, as disclosed in U.S. patent application Ser. No. 456,611, filed herewith at even date, and incorporated herein by reference.

The following examples are offered by way of illustration only are by no means intended to limit the scope of the claimed invention. In these examples, all percentages are by weight if for solids and by volume if for liquids, unless otherwise noted, and all temperatures are given in degrees Celsius.

EXAMPLE 1

Purification of *Thermus thermophilus* DNA Polymerase

This example describes the isolation of Tth DNA polymerase from *Thermus thermophilus*. Tth DNA polymerase was assayed at various points during purification according to the method described for Taq polymerase in Lawyer et al., 1989, *J. Biol. Chem.* 264(11):6427–6437, incorporated herein by reference.

Typically, this assay is performed in 50 µd of a reaction mixture composed of 25 mM TAPS-HCl, pH 9.5 (20° C.); 50 mM KCl; 2 mM $MgCl_2$; 1 mM β- mercaptoethanol; 200 µM in each of dATP, dGTP, and TTP; 100 µM $\alpha$-$^{32}$P-dCTP (0.03 to 0.07 µCi/nmol; 12.5 µg of activated salmon sperm DNA; and polymerase. The reaction is initiated by addition of polymerase in diluent (diluent is composed of 10 mM Tris-HCl, pH 8.0, 50 mM KCl, 0.1 mM EDTA, 1 mg/ml autoclaved gelatin, 0.5% NP40, 0.5% Tween 20, and 1 mM β- mercaptoethanol), and the reaction is carried out at 74° C. After a 10 minute incubation, the reaction is stopped by adding 10 µl of 60 mM EDTA. The reaction mixture is centrifuged, and 50 µl of reaction mixture is transferred to 1.0 ml of 50 µg/ml carrier DNA in 2 mM EDTA (at 0° C.). An equal volume (1 ml) of 20% TCA, 2% sodium pyrophosphate is added and mixed. The mixture is incubated at 0° C. for 15 to 20 minutes and then filtered through Whatman GF/C filters and extensively washed (6×5 ml) with a cold mixture containing 5% TCA and 1% pyrophosphate, followed by a cold 95% ethanol wash. The filters are then dried and the radioactivity counted. Background (minus enzyme) is usually 0.001% to 0.01% of input cpm. About 250 to 500 pmol of $^{32}$P-dCTP standard is spotted for unit calculation. One unit is equal to 10 nmoles dNTP incorporated in 30 minutes at 74° C. Units are calculated as follows.

$$\frac{\text{sample } cpm - \text{enzyme } dil.\ cpm}{\text{specific activity of } dCTP(cpm/pmole)} = pmole\ incorporated$$

$$\frac{pmole\ incorporated \times 3 \times \text{dilution factor} \times 4}{4.167 \times 10} = units/ml$$

Enzyme activity is not completely linear with time. With purified enzyme, a thirty minute assay is usually 2.5× a 10 minute assay.

About 202 g of frozen *Thermus thermophilus* strain HB8 cells (ATCC No. 27,634) were thawed in 100 ml of 3× TE-DTT buffer (150 mM Tris-Cl, pH 7.5, 3 mM EDTA, and 3 mM dithiothreitol) containing 2.4 mM PMSF (from 144 mM stock in DMF) and homogenized at low speed in a blender. All operations were carried out at 0° to 4° C. unless otherwise stated. All glassware was baked prior to use, and solutions used in the purification were autoclaved, if possible, prior to use. The thawed cells were lysed in an Aminco French pressure cell (18,000 psi), then diluted with an equal volume of 1× TE-DTT buffer containing 2.4 mM PMSF and sonicated to reduce viscosity (⅓ aliquots, 80% output, 10 minutes, 50% duty cycle). The lysate was diluted with additional 1× TE-DTT buffer containing fresh 2.4 mM PMSF to final 5.5× cell wet weight The resulting fraction, fraction I (1,100 ml), contained 15.6 g of protein and 46.8×10$^4$ units of activity.

Ammonium sulfate was added to 0.2M (29.07 g) and the lysate stirred for 30 minutes on ice. Upon the addition of the ammonium sulfate, a precipitate formed which was not removed prior to the PEI precipitation step, described below. Ammonium sulfate prevents the Tth polymerase from binding to DNA in the crude lysate and reduces ionic interactions of the DNA polymerase with other cell lysate proteins. Speed in the initial steps of purification (i.e., up to loading onto and eluting from the phenyl-sepharose column) and the presence of protease inhibitor (PMSF at 2.4 mM) are important for protection from proteolytic degradation of the DNA polymerase. For best results, then, one proceeds directly to the Polymin P (purchased from BDH) precipitation step to remove most nucleic acids rather than introducing a centrifugation step to remove the precipitate that forms upon the addition of ammonium sulfate. For the same reason, one can include in fraction II the soft, viscous pellet that forms on top of the Polymin P/ammonium sulfate pellet, because the viscous pellet does not contain nucleic acids. Agarose gel electrophoresis and ethidium bromide staining of the Polymin P supernatant indicates that >90% of the macromolecular DNA and RNA is removed by 0.2% Polymin P. To account for the additional amount of protein, when the viscous pellet is included, the phenyl sepharose column should then be ~10% larger than described below.

Empirical testing showed that 0.2% Polymin P (polyethyleneimine, PEI) precipitates ≧90% of the total nucleic acid. Polymin P (pH 7.5) was added slowly to 0.2% (22 ml of 10% PEI) and the slurry stirred one hour on ice, then centrifuged at 30,000×g at 4° C. for 45 minutes. A soft, viscous pellet formed on top of the PEI pellet, requiring additional centrifugation after 920 ml of the supernatant was decanted. The viscous material was centrifuged for one hour at 186,000×g at 2° C. and yielded an additional 40 ml of supernatant and very large gelatinous pellets. These pellets contained <2% of the activity present in fraction I and 1.96 g of protein or 12.5% of fraction I. The supernatants were pooled (fraction II, 960 ml) and contained 10.5 g protein and $42.6 \times 10^4$ units of activity.

Fraction II was loaded onto a 3.2×6.5 cm (52 ml) phenyl sepharose CL-4B (Lot MI 02547, purchased from Pharmacia-LKB) column (equilibrated in TE containing 0.2M ammonium sulfate and 0.5 mM DTT) at 80 ml/hr (10 ml/cm$^2$/hr). All resins were equilibrated and recycled according to the manufacturer's recommendations. The column was washed with 240 ml of the same buffer ($A_{280}$ to baseline), then with 220 ml TE containing 0.5 mM DTT (no ammonium sulfate) to remove non-Tth DNA polymerase proteins. The column was then washed with 270 ml of 20% ethylene glycol in TE containing 0.5 mM DTT to remove more contaminating protein, and the Tth polymerase activity was eluted with 2M urea in TE containing 20% ethylene glycol and 0.5 mM DTT. The fractions (5 ml) containing the polymerase activity were pooled (fraction IIIa, 84 ml). The routine activity assays of the flow-through and wash fractions revealed that only ~50% of the applied polymerase activity had bound when the capacity of the column was exceeded. To avoid exceeding the capacity of the column, a larger column (with, for example, at least 2× as much phenyl sepharose) should be used. The flow-through and wash fractions containing the balance of the activity were pooled (fraction IIb, 685 ml), adjusted to 0.2M ammonium sulfate, and then reapplied to the same column after the column had been recycled and reequilibrated.

Assays of low levels of Tth DNA polymerase activity in fractions containing Polymin P (e.g., phenyl sepharose flow-through fractions) should be conducted in the presence and absence of 10 mM EDTA. The presence of EDTA permits correction for elevated background levels of radioactivity due to Polymin P binding of the nucleotide triphosphate substrate.

As noted above, the Tth polymerase activity was eluted with a 2M urea step (fraction IIIa). The eluant was dialyzed into heparin sepharose loading buffer to avoid prolonged exposure to urea (to avoid carbamylation) while waiting for the unretained fraction IIb to be rerun over the same phenyl sepharose column. The dialyzed fraction IIIa contained 42% of the applied activity (179,213 units) and about 3.5% of the applied protein (351 mg), yielding a 12-fold purification. The pooled flow-through and 0.2M ammonium sulfate wash fractions containing the unbound Tth DNA polymerase (fraction IIb) consisted of 42.6% of the applied activity (181,559 units) and 40.8% of the applied protein (4,110 mg). The column was recycled as recommended by the manufacturer, reequilibrated with the starting buffer, and fraction IIb was reapplied.

Fraction IIb was loaded onto the phenyl sepharose column at 78 ml/hr. The column was washed with 270 ml of 0.2M ammonium sulfate in TE containing 0.5 mM DTT, then with 170 ml TE containing 0.5 mM DTT (no ammonium sulfate), and finally with 260 ml of 20% ethylene glycol in TE containing 0.5 mM DTT. The Tth polymerase activity was again eluted with 2M urea in TE containing 20% ethylene glycol and 0.5 mM DTT. The fractions (4.3 ml) containing the polymerase activity were pooled (fraction IIIb). The 2M urea eluate (fraction IIIb) contained 87.6% of the applied activity (159,132 units) and 8.8% of the applied protein (363 mg), yielding a 9.7 fold purification.

Fraction IIIb (116.4 ml) was adjusted to 0.15M KCl and pooled with fraction IIIa, which had been dialyzed without loss of activity into a buffer composed of 50 mM Tris-Cl, pH 7.5, 0.1 mM EDTA, 0.2% Tween 20, 0.5 mM DTT, and 0.15M KCl and stored at 4° C. The pooled fraction III (243 ml) contained substantial levels of contaminating specific and non-specific Tth endonucleases and exonucleases. The combined fraction III contained 326,009 units of activity and 705 mg protein.

Fraction III was loaded onto a 2.2×12 cm (45 ml) heparin sepharose CL-6B (purchased from Pharmacia-LKB) column and equilibrated in 0.15M KCl, 50 mM Tris-Cl, pH 7.5, 0.1 mM EDTA, 0.2% Tween 20, and 0.5 mM DTT) at 45 ml/hr. All of the applied activity was retained by the column. The column was washed with 175 ml of the same buffer ($A_{280}$ to baseline) and eluted with 670 ml of a linear 150–750 mM KCl gradient in the same buffer. Fractions (5.25 ml) eluting between 0.31 and 0.355M KCl were pooled (fraction IV, 149 ml). Similar to Taq DNA polymerase, which elutes with a peak at 0.31M KCl, Tth DNA polymerase elutes with a peak at 0.33M KCl contaminated with the coeluting TthHB8I endonuclease (an isoschizomer of TaqI endonuclease [TCGA]).

Fraction IV was concentrated ~10-fold on an Amicon YM30 membrane and subsequently dialyzed against 25 mM Tris-Cl, pH 7.5, 0.1 mM EDTA, 0.2% Tween 20, 0.5 mM DTT, and 100 mM KCl. A precipitate formed during dialysis and was removed by centrifugation (10 minutes at 12,000×g, 4° C.) without loss of activity. These steps, including the heparin sepharose column, yielded a 27-fold purification, with 95% of the activity applied to the heparin-sepharose column being recovered.

Although Tth DNA polymerase shares 88% sequence identity (93% similarity) with Taq DNA polymerase, the ~10% difference in the two proteins changes their purification properties on phosphocellulose significantly. In contrast to Taq DNA polymerase, which, when run in pH 7.5 Tris buffer, elutes at 0.2M KCl from phosphocellulose with its contaminating endonuclease eluting at ~0.6–0.8M KCl, Tth DNA polymerase and endonuclease cannot be easily separated on phosphocellulose. Tth DNA polymerase elutes with a peak at ~0.45M KCl and the Tth endonuclease peak is at 0.58M KCl. Affigel-blue (Biorad Laboratories), however, is a useful resin for separating Tth endonuclease from Tth DNA polymerase. Affigel blue is a dye-ligand resin used for affinity purification of enzymes with binding sites for nucleotides.

The supernatant from centrifugation of fraction IV (16.8 ml) was loaded onto a 1.6×10 cm (20 ml) affigel-blue column (equilibrated in 25 mM Tris-Cl, pH 7.5, 0.1 mM EDTA, 0.2% Tween 20, 0.5 mM DTT, and 100 mM KCl) at 20 ml/hr. All of the applied Tth DNA polymerase activity bound to the resin. The column was washed with 30 ml of the same buffer ($A_{280}$ to baseline) and eluted with a 300 ml linear 0.1–0.5M KCl gradient in the same buffer. Fractions (3.05 ml) eluting between 0.28 and 0.455M KCl were assayed to ensure absence of contaminating double- and single-strand endonuclease, indicated by absence of both lower molecular weight specific or non-specific DNA fragments after one hour or eleven hours incubation at 60° C. with 5–20 units of Tth polymerase activity using 600 ng of plasmid pLSG1 covalently-closed circular DNA or 850 ng of M13mp18 SS-DNA. When the KCl gradient was applied, the Tth polymerase eluted with a fairly broad peak at ~0.35M KCl, while the endonuclease seemed to elute at >0.5M KCl. Washing the affigel-blue column with 0.15M KCl and eluting with a linear 0.15–0.6M KCl gradient may provide better separation.

Based on the SDS-PAGE pattern, two pools were made: fraction Va from peak fractions (61 ml) and fraction Vb, from flanking fractions (72.5 ml). Fraction Va contained $22.2 \times 10^4$ units of activity and 5.5 mg of protein, and fraction Vb contained $5.2 \times 10^4$ units of activity and 3.5 mg of protein. Both pools were concentrated separately by diafiltration on YM30 membranes. Fraction Vb was concentrated ~10-fold on an Amicon YM30 membrane, then dialyzed into CM-Trisacryl buffer (25 mM sodium acetate buffer, pH 5.0, 0.5 mM DTT, 0.1 mM EDTA, and 0.2% Tween 20) containing 50 mM NaCl. Again, a precipitate formed during dialysis and was removed by centrifugation (12,000×g for 10 minutes at 4° C.) resulting in a minor (<2%) loss of activity and a 1.4-fold purification. The resulting supernatant (8.6 ml, $5.1 \times 10^4$ units of activity and 2.3 mg of protein) was loaded onto a 1×3.8 cm (3 ml) CM-Trisacryl column (equilibrated in CM-Trisacryl buffer and 50 mM NaCl) at 3 ml/hr. All of the applied activity was retained by the column. The column was washed with 17 ml of the same buffer and eluted with 50 ml of a steep, linear 0.05–0.7M NaCl gradient in the same buffer. Fractions (1 ml) eluting between 0.175 and 0.25M were analyzed by SDS-PAGE electrophoresis prior to being pooled with fraction Va. The Tth DNA polymerase activity eluted with a sharp peak at 0.21M NaCl. Judged by SDS-page of the gradient fractions, the polymerase was significantly enriched but still contained major contaminating bands at ~35 kDa, ~25 kDa, and ~18 kDa. The resulting fraction V (11.4 ml), which contained fraction Va and the peak fractions from the CM-Trisacyl column treatment of Fraction Vb, was dialyzed into CM-Trisacryl buffer containing 50 mM NaCl. More precipitate formed and was removed by centrifugation (10 minutes at 12,000×g, 4° C.) with insignificant loss of activity. The precipitate contained 0.91 mg protein (~20%) and 2,227 units of activity (<1 %).

The resulting supernatant (12.8 ml, containing 5.18 mg protein and $24.8 \times 10^4$ units of activity) was loaded onto a 1.6×6.0 cm (12 ml) CM-Trisacryl (purchased from Pharmacia-LKB) column (equilibrated in CM-Trisacryl buffer containing 50 mM NaCl) at 12 ml/hr. The column was washed with 20 ml of the same buffer containing 50 mM NaCl, then with 27 ml of the same buffer containing 100 mM NaCl. No detectable polymerase activity appeared in the flow-through fractions. A technical problem (column adaptor broke) led to the immediate elution (in 400 mM NaCl) of the activity when the 100–400 mM NaCl linear gradient was applied. Seventy-eight percent of the applied activity ($19.4 \times 10^4$ units and 4.09 mg protein) was recovered and reapplied to a CM-Trisacryl column of the same dimensions.

The loading fraction (35 ml) was 2.7-fold diluted after readjusting the solution to 50 mM NaCl. The column was washed with 33 ml of the same buffer and eluted with a 180 ml linear 50–400 mM NaCl gradient in the same buffer. Fractions (1.4 ml) eluting between 0.16 and 0.2M NaCl were separately concentrated/diafiltered on Centricon 30 membranes in 2.5× storage buffer (50 mM Tris-Cl, pH 7.5, 250 mM KCl, 0.25 mM EDTA, 2.5 mM DTT, and 0.5% Tween 20 |Pierce, Surfact-Amps|). The Tth DNA polymerase activity eluted with a peak at 0.183M NaCl, slightly earlier than was observed in the trial column. In comparison, Taq DNA polymerase elutes at 0.19–0.205M NaCl when run on CM-Trisacryl in the same pH 5.0 sodium acetate buffer. The concentrated and diafiltered samples were diluted with 1.5 volumes of 80% glycerol (Fisher, spectral grade, autoclaved) and stored at −20° C. until completion of the analysis of the individual fractions by SDS-PAGE. The fractions containing the Tth polymerase were of similar purity (~85–90%), as determined by SDS-PAGE gel electrophoresis. The major band migrates as a ~90 kDA protein in this gel system with minor contaminating bands. The discrepancy between this observed molecular weight (~90 kDa) and the calculated molecular weight (~94 kDa, from the gene sequence) may simply be due to anomalous gel migration or to degradation during the purification process. The staining patterns of the individual fractions were similar enough to allow pooling of all of the fractions (fraction VI, 21.5 ml).

Fraction VI was further concentrated/diafiltered on an Amicon YM30 membrane in 2.5× storage buffer. When the volume measured 7 ml, 0.2 ml were removed for amino acid composition and sequence analysis. The remaining 6.8 ml were concentrated to 1.6 ml and diluted with 2.4 ml of 80% glycerol. The resulting final pool (4 ml) contained 2.17 mg protein and 162,789 units of activity (34.8% yield) with a specific activity of 75,018 units/mg protein. The results of each step of the purification are presented in tabular form below.

TABLE I

|  | Volume (ml) | Protein mg/ml | Protein mg total | Enzyme Activity units/ml | Enzyme Activity units total | Yield % | Specific Activity units/mg | Fold purification |
|---|---|---|---|---|---|---|---|---|
| Fraction I | 1100 | 14.2 | 15,620 | 425.7 | 468,200 | 100 | 30 |  |
| pellet from Fraction I | 110 | 17.8 | 1,958 | 84.4 | 9,284 |  |  |  |
| Fraction II | 960 | 10.5 | 10,080 | 444.0 | 426,240 | 91.0 | 42 | 1.4 |
| Fraction II (pool) | 243 | 2.9 | 705 | 1,341.6 | 326,009 | 69.6 | 463 | 15.4 |
| Fraction IIIa (after dial.) | 121 | 2.9 | 351 | 1,481.1 | 179,213 | (38.3) | 551 | 17.0 |
| Fraction IIb | 685 | 6.0 | 4,110 | 265.1 | 181,554 | (38.8) | 44 | 1.5 |
| Fraction IIIb | 117 | 3.1 | 363 | 1,360.1 | 159,132 | (34.0) | 439 | 14.6 |
| Fraction IV (before conc.) | 149 | 0.25 | 37.3 | 2,123.2 | 316,357 | 67.6 | 8493 | 283 |
| ppt. from Fraction IV | 1.7 | 6.2 | 10.5 | 3,038.9 | 5,166 |  |  |  |
| Fraction IV (Affigel load) | 16.8 | 1.46 | 24.5 | 18,419.8 | 309,452 | 66.1 | 12,616 | 420 |
| Fraction V (pool, undialyzed) | 11.4 | 0.48 | 5.47 | 23,142.9 | 263,929 | 56.3 | 48,214 | 1,607 |
| Fraction Va (conc.) | 7.4 | 0.52 | 3.85 | 29,996.4 | 221,973 | (47.4) | 57,685 | 1,923 |
| Fraction Vb (conc. + dialyzed) | 8.75 | 0.265 | 2.32 | 5,748.9 | 50,618 | (10.8) | 21,830 | 728 |
| Fraction V (CM II load) | 12.8 | 0.405 | 5.18 | 19,440.0 | 248,832 | 53.1 | 48,000 | 1,600 |
| CM III load | 35 | 0.117 | 4.09 | 5,563.5 | 194,723 | 41.6 | 47,551 | 1,585 |
| Fraction VI | 7 | 0.31 | 2.17 | 23,255.6 | 162,789 | 34.8 | 75,018 | 2,501 |

EXAMPLE 2

Cloning the *Thermus thermophilus* Tth DNA Polymerase Gene

This Examples describes the strategy and methodology for cloning the Tth DNA polymerase (Tth Pol) gene of *Thermus thermophilus*. PCR-amplified fragments of the T.

*aquaticus* DNA polymerase (Taq Pol) gene were used to probe genomic DNA blots to determine the restriction sites present in the Tth Pol gene and flanking regions. PCR amplification of the Tth Pol gene with Taq pol-specific primers provided even more restriction site and DNA sequence information about the Tth Pol gene. This information provided the basis for a two-step cloning procedure to isolate the Tth Pol gene into plasmid pBS 13+(marketed by Stratagene; the plasmid is also known as BSM13+).

A. Preparation of Probes

Four labeled probes were generated by PCR in the presence of biotinylated dUTP (biotin-11-dUTP, purchased from Bethesda Research Laboratories) and *Thermus aquaticus* DNA to probe southern blots of *T. thermophilus* genomic DNA. Probe A was generated with primers CM07 (Seq ID No. 1) and EK194 (Seq ID No. 2) and encompasses 438 bp of the 5' end of the Taq polymerase gene from nucleotide −230 to +207. Probe B was generated with primers MK138 (Seq ID No. 6) and MK124 (Seq ID No. 3) and encompasses 355 bp that span the HindIII site of the Taq Pol gene and extend from nucleotide +555 to +879. Probe C was generated with primers MK143 (Seq ID No. 7) and MK131 (Seq ID No. 5) and encompasses 579 bp of the template-primer binding site coding sequence and the BamHI site of the Taq Pol gene from nucleotide +1313 to +1891. Probe D was generated with primers MK130 (Seq ID No. 4) and MK151 (Seq ID No. 8) and encompasses 473 bp of the 3' end of the Taq Pol gene from nucleotide +2108 to +3384.

The sequences of the primers used to prepare the probes are shown below:

|       | Seq ID No. | Sequence                    |
|-------|------------|-----------------------------|
| CM07  | 1          | 5'-GCGTGGCGGCGGAGGCGTTG     |
| EK194 | 2          | 5'-CTTGGCGTCAAAGACCACGATC   |
| MK124 | 3          | 5'-GGCCTTGGGGCTTTCCAGA      |
| MK130 | 4          | 5'-TGCGGGCCTGGATTGAGAAG     |
| MK131 | 5          | 5'-CCCGGATCAGGTTCTCGTC      |
| MK138 | 6          | 5'-GACCGGGGACGAGTCCGAC      |
| MK143 | 7          | 5'-CCGCTGTCCTGGCCCACATG     |
| MK151 | 8          | 5'-TTCGGCCCACCATGCCTGGT     |

The sequence of the Taq Pol gene is disclosed in Lawyer et al. and in U.S. patent application Ser. No. 143,441, filed Jan. 12, 1988, both incorporated herein by reference.

The probes were individually prepared in 100 μl of total reaction mixture composed of 10 mM Tris-HCl, pH 9.0 (the pH was set at nine to counteract the pH of the biotinylated dUTP in the reaction mixture; the biotinylated dUTP is in a buffer of 150 mM Tris, pH 7.4), 50 mM KCl, 1.0 mM MgCl$_2$, 100 μg/ml gelatin, 2 U of Taq Pol (manufactured by Hoffmann-La Roche, Inc., and marketed by Perkin Elmer, Norwalk, Conn.), 50 μM dATP, 50 μM dCTP, 50 μM dGTP, 37.5 μM TTP, 12.5 μM biotin-11-dUTP, 50 pmol each primer and template DNA. The template DNA consisted of 1 μl of a 1:100 dilution of PCR products generated with the same primers in 25 cycles of a polymerase chain reaction in a reaction mixture composed of 10 mM Tris-HCl, pH 8.3; 1.5 mM MgCl$_2$; 200 μM each dNTP; no biotinylated dUTP; and 1.0 ng Taq genomic DNA boiled for three minutes and then quickly cooled on ice. PCR was performed in a Perkin Elmer Thermal Cycler. Probes and the template for probe generation were generated using 15 cycles of a 1 minute 45 second ramp to 98° C., 15 seconds at 98° C. (in-tube temperature of 96.5° C.), 45 second ramp to 55° C., 20 seconds at 55° C., 45 second ramp to 72° C., and 30 seconds at 72° C. There was a 5 minute soak at 72° C. at the end of the last cycle.

The genomic DNA hybridized to the probes was isolated as described in Lawyer et al., and Southern blots were performed as described by Maniatis, except that MSI Magnagraph™ nylon membrane was used rather than nitrocellulose, and the DNA was fixed to the membrane with UV light (in a UV Stratalinker™ 1800, marketed by Stratagene) rather than heat.

Blots were prehybridized at 42° C. for 2 hours in a solution composed of 5× SSPE, 5× Denhardt's solution, 0.5% SDS, 5% dextran sulfate, 150 μg/ml carrier DNA, and 50% formamide. Hybridization of probes to the blots was carried out overnight at 42° C. in the same solution with probe present at approximately 10 ng/ml. After hybridization, the membranes were washed to remove unbound probe.

Each of the four probes A-D hybridized to *Thermus thermophilus* genomic DNA. A restriction site map of the Tth Pol gene region of the genome was constructed by individually digesting and probing Southern blots of the digested Tth genomic DNA with restriction enzymes PstI, BamHI, SacII, and Asp718. In addition, double digestions with HindIII/Asp718, HindIII/BstEII; HindIII/NheI; BamHI/Asp718; BamHI/BstEII; BamHI/SphI; and BamHI/NheI of Tth genomic DNA followed by Southern blotting and probing of the digested DNA were performed. The resulting information allowed the construction of a restriction site map used in the cloning of the Tth Pol gene.

B. PCR Amplification of the Primer—Template Binding Site Region of the Tth Pol Gene A series of PCR amplifications was carried out using Tth genomic DNA as template and primers homologous to *Thermus aquaticus* DNA in the region of the Taq Pol gene that encodes the primer-template binding site sequence of Taq Pol. Several primer pairs in various combinations were used in the amplifications, which were targeted to amplify the region from nucleotide 293 to 1891 of the Taq Pol gene. One primer pair, MK143 (Seq ID No. 7) and MK131 (Seq ID No. 5), yielded product.

The amplification reactions were carried out in a buffer composed of 10 mM Tris-HCl, pH 8.3, 50 mM KCl, 1.5 mM MgCl$_2$, 200 μM each dNTP, 2 U Taq Pol, 1 ng heat-denatured Tth genomic DNA, and 50 pmol of each primer. The amplifications were carried out for 25 cycles using the same thermocycler programming described above, and PCR products were analyzed via polyacrylamide gel electrophoresis.

Most of the primers used in the unsuccessful amplifications either had many mismatches when later compared with the Tth Pol gene sequence or had strategic mismatches at the 3' end of the primer. Primer MK143 (Seq ID No. 7) had 3 mismatches to the Tth Pol gene sequence but those mismatches were located at the 5' end of the primer and were followed by 15 bases of homology. Primer MK131 (Seq ID No. 5) had 2 mismatches to the Tth Pol gene, but the mismatches were located in the middle of the primer.

The product of the MK143/MK131 (Seq ID No. 7/Seq ID No. 5) amplification of Tth genomic DNA migrated on a polyacrylamide gel identically with the MK143/MK131

(Seq ID No. 7/Seq ID No. 5) amplification product using Taq genomic DNA as template. Restriction mapping of these Taq and Tth amplification products show identical BamHI, SacI, and XhoI restriction sites but different SacII and PstI restriction sites. The Tth PCR product generated with primers MK143 (Seq ID No. 7) and MK131 (Seq ID No. 5) was further amplified via asymmetric PCR with the same primers and subjected to DNA sequence analysis in accordance with the methods described in Gyllensten and Erlich, 1988, Proc. Natl. Acad. Sci. USA 85(20):7652-7656; U.S. application Ser. No. 248,896, filed Sep. 23, 1988; Innis et al., 1988, Proc. Natl. Acad. Sci. USA 85:9436-9440; and U.S. application Ser. No. 249,637, filed Sep. 23, 1988, incorporated herein by reference.

C. Coning the 5' End of the Tth Pol Gene

From the restriction site map and sequence information generated by the Southern blot and PCR analyses, a strategy for cloning the Tth Pol gene in two steps was developed. An ~3 kb HindIII fragment of Tth genomic DNA hybridized with probes A, B, and C but not D, indicating that the fragment contains the 5' end of the Tth Pol gene. This ~3 kb HindIII fragment also contained a BamHI restriction site, which proved useful in cloning the 5' end of the gene.

To clone the 5' end of the Tth Pol gene, a HindIII digest of Tth genomic DNA was size fractionated by electroelution on a 0.5 inch tube gel by collecting 250 µl fractions every 5 minutes during electrophoresis as fragments of about 3 kb in size were eluting from the gel. Dot blots with the probes described above identified the fractions containing the restriction fragments of interest. The fractionated DNA of interest was then digested with restriction enzyme BamHI and treated with calf-intestine alkaline phosphatase (CIAP). CIAP was purchased from Boehringer Mannheim and used as directed by the manufacturer. Restriction enzymes, E. coli DNA polymerase, and ligase enzymes used in these Examples can be purchased from manufacturers such as New England Biolabs, Boehringer Mannheim (Asp718), and Promega (Csp45I, an isoschizomer of AsuII) and used as directed by the manufacturer.

Plasmid pBS 13+(purchased from Stratagene) was likewise digested with restriction enzymes HindIII and BamHI and then ligated with the BamHI digested, CIAP-treated ~3 kb HindIII fragment pool. The ligation mixture was used to transform E. coli K12 strain DG 98 (thi-1, endA1, hsdR17, lacIQ, lacZΔM15, proC::Tn10, supE44/F', lacIQ, lacZΔM15, proC+, available from the ATCC under accession number 39,768) in substantial accord with the procedure of Hanahan et al. The ampicillin resistant (AmpR) transformants were screened by failure to exhibit blue color on X-gal plates and by probe hybridization with the DNA of transformed cells (via replica plating and lysis of the replicated cells as described by Woods et al., 1982, Proc. Natl. Acad. Sci. USA 79:5661) with $^{32}$P-labeled (by kinase treatment with γ-$^{32}$P-ATP) primer MK143 (Seq ID No. 7). One colony contained a plasmid, designated pBSM:Tth5' ; in which the ~2.5 kb HindIII-BmHI restriction fragment had ligated with the large HindIII-BamHI restriction fragment of plasmid pBS 13+.

D. Cloning the 3' End of the Tth Pol Gene

The 3' end of the Tth Pol gene was inserted into plasmid pBSM:Tth5' to yield a vector, designated pBSM:Tth, that contains the intact coding sequence of the Tth Pol gene. The Southern blot and DNA sequence information showed that an ~12 kb BamHI fragment of Tth genomic DNA could be digested with Asp718 to yield an ~5.6 kb fragment that hybridized with Probe D (the fragment should also hybridize with Probe C). The information also showed that the BamHI site used to create the ~5.6 kb BamHI-Asp718 restriction fragment was the same BamHI site used to create the ~2.5 kb HindIII-BamHI restriction fragment in plasmid pBSM:Tth5'.

Tth genomic DNA was then digested to completion with restriction enzyme BamHI and size-fractionated as described above, except that fractions containing fragments of ~12 kb in size were identified and collected. Fractions which hybridized in a dot blot to biotinylated Probes D and C were pooled, digested with restriction enzyme Asp718, treated with CIAP, and ligated with BamHI-Asp718 digested plasmid pBSM:Tth5'. The ligated DNA was transformed into E. coli K12 strain DG101 (thi-1, endA1, hsdR17, lacIQ, lacZΔM15, proC::Tn10).

The AmpR transformants were screened as above with $^{32}$P-labeled primer MK132 to identify several colonies that contained a plasmid, designated pBSM:Tth, that contained the ~5.6 kb BamHI-Asp718 and ~2.5 kb HindIII-BamHI fragments in the correct orientation to reconstruct an intact coding sequence of the Tth Pol gene. The sequence of oliognucleotide MK132 perfectly matches the Tth Pol gene sequence. Several colonies with plasmid DNA that hybridized to the probe and yielded the expected fragments on restriction enzyme digestion were induced with IPTG, and Western blot analysis of protein samples from induced and uninduced colonies with Taq Pol polyclonal antibody showed an IPTG inducible band the same size (~94 kDa) as Taq Pol. One such colony was deposited with the ATCC and can be obtained from the ATCC under accession number ATCC No. 68195. When culturing the strain, one must maintain selective pressure (ampicillin) to prevent loss of plasmid DNA. ATCC No. 68195 can thus also be used to obtain untransformed DG101 cells.

EXAMPLE 3

Construction of Plasmid pLSG21

The deletion of 3' noncoding ("downstream") sequences has been shown to enhance recombinant expression of Thermus DNA polymerase in E. coli. In pBSM:Tth, double digestion with restriction enzymes BstEII and KpnI followed by Klenow repair in the presence of all four dNTPs and ligation under dilute conditions to favor intramolecular ligation results in the deletion of 3' noncoding sequences of the Tth DNA Pol gene. Restriction enzyme BstEII cuts plasmid pBSM:Tth in the 3' noncoding region of the Tth Pol gene, and restriction enzyme KpnI cuts in the polylinker region of the vector.

This deletion was made, and the resulting plasmid was designated as plasmid pLSG21. The deletion protocol results in the regeneration of the BstEII restriction site. However, plasmid pLSG21 does not drive increased levels of Tth Pol expression when compared to the levels achieved in plasmid pBSM:Tth-transformed E. coli host cells.

EXAMPLE 4

Construction of Plasmids pLSG22, pLSG23, and pLSG24

The Tth Pol gene lacks convenient restriction sites at the 5' and 3' ends of the gene. Such restriction sites facilitate the construction of a wide variety of expression vectors. In addition, codons at the 5' end of the coding sequence are highly GC-rich, which may inhibit efficient translation initiation and expression in *E. coli*. Site-directed mutagenesis with oligonucleotides can be, and has been, used to introduce a number of useful changes in the coding sequences and in the 5' and 3' noncoding regions of the Tth Pol gene.

Plasmid pBS13+derivatives, such as plasmid pBSM:Tth, can be obtained in single-stranded form by the protocols described in Lawyer et al. and by Stratagene, the commercial supplier of plasmid pBS13+. To make single-stranded plasmid pBS13+or a single-stranded derivative plasmid, a host cell transformed with the plasmid is infected with a helper phage (such as R408) and cultured under conditions that allow production of phage DNA. The phage DNA is then collected and comprises the desired single-stranded DNA and a small amount of helper phage DNA. The desired DNA can be purified to remove the helper phage DNA by separating the DNA based on size, i.e., by electroelution.

For the constructions described below, a plasmid, designated pBSMΔPvuII, proved useful. Plasmid pBSMΔPvuII was generated by deletion of the 382 bp PvuII fragment of plasmid pBS13+. The site-specific mutagenesis protocols involved the following steps: (1) single-stranded plasmid pBSM:Tth (or other pBS13+single-stranded derivative) and double-stranded, PvuII digested plasmid pBSMΔPvuII were annealed by boiling a 1 to 2.5 molar ratio of pBSM:Tth (or other plasmid pBS13+derivative)/pBSMΔPvuII for three minutes in Klenow salts and then incubating the resulting mixture at 65° C. for 5 minutes; (2) kinased mutagenizing oligonucleotide was then annealed to the resulting gapped duplex at a molar ratio of 5 to 1 by heating the oligonucleotide to 95° C. for 1 minute and then adding the oligonucleotide to the gapped duplex mixture held at 75° C.; (3) the resulting mixture was incubated at 75° C. for 2 minutes and then slowly cooled to room temperature; (4) this annealed mixture was then extended with Klenow enzyme in the presence of all four dNTPs (200 µM in each dNTP) for 15 minutes at 37° C. with the addition of ligase and 40 µM ATP to the reaction. The resulting mixture was used to transform *E. coli* K12 DG101.

The AmpR transformants were screened by probing with the appropriate screening primer. Colonies that had plasmid DNA that hybridized to the probe were expanded into 3 ml cultures in R66 media (0.6% beef extract, 0.6% yeast extract, 2% peptone, 0.5% NaCl, 40 mM KPO$_4$, pH 7.2, 0.2% glucose, and 100 µg/ml ampicillin), incubated at 37° C. for eight hours, and then used to prepare plasmid DNA by the method of Birnboim and Doly. The resulting plasmid DNA was subjected to restriction enzyme and DNA sequence analysis to ensure that the desired plasmid was obtained.

A. Construction of Plasmid pLSG22

EcoRV and BglII restriction enzyme sites were introduced downstream of the TGA stop codon of the Tth Pol gene coding sequence by the foregoing method using oligonucleotide DG122 (Seq ID No. 9) to mutagenize plasmid pBSM:Tth and oligonucleotide DG123 (Seq ID No. 10) to identify the desired transformants by probe hybridization. These oligonucleotides are shown below:

|       | Seq ID No. |                                                                        |
|-------|------------|------------------------------------------------------------------------|
|       |            |                         BglII            EcoR V                        |
| DG122 | 9          | 5' CCTCTAAACGGCAGATCTGATATCAACCCTTGGCGGAAAGC 3'                        |
| DG123 | 10         | 5' CAGATCTGATATCAACCC                                                  |

The resulting plasmid was designated pLSG22.

B. Construction of Plasmid pLSG23

Plasmid pLSG22 was mutagenized to introduce BstXI and AseI (Csp45I) restriction sites at the ATG start codon of the coding sequence of the Tth Pol gene. In addition, codons 2, 3, and 5–7 were altered to be more AT-rich without changing the amino acid sequence of the resulting protein. The mutagenizing oligonucleotide was DG189 (Seq ID No. 13), depicted below:

|             |       |                    |          --BstXI--         |              |
|-------------|-------|--------------------|----------------------------|--------------|
| Seq ID No. 13) |    | AsuII              | AseI                       |              |
| DG189       | 5'CCGGCCTTTGGGTTCGAATAATGGTAACATAGCTCCCATTAATTTGGGCCACCTGTCCCCG 3' |
| Tth         |       |                    | TTCAAAGAGCGGAAGCATCGCCTCCAT | (Seq ID No. 12) |
| Codon       |       |                    | 9 8 7 6 5 4 3 2 1          |              |

The resulting plasmid was designated pLSG23. Transformants harboring plasmid pLSG23 were identified by their AmpR phenotype and by hybridization with oligonucleotide DG118 (Seq ID No. 11), which has the structure shown below:

DG118 Seq ID No. 11 5'TGGTAACATAGCTTCCAT 3'

C. Constriction of Plasmid pLSG24

Plasmid pLSG22 was mutagenized to introduce BstXI and NdeI restriction sites at the ATG start codon of the coding sequence of the Tth Pol gene. In addition, codons 2, 3, and 5–7 were altered to be more AT-rich without changing the amino acid sequence of the encoding protein. The mutagenizing oligonucleotide was DG190 (Seq ID No. 14), depicted below.

```
                                                        -BstXI----
(Seq ID No. 14)       AsuII                             NdeI
DG190  5'CCGGCCTTTGGGTTCGAATAATGGTAACATAGCTTCCATATGTTTGGGCCACCTGTCCCCG 3'
Tth                              TTCAAAGAGCGGAAGCATCGCCTCCAT (Seq ID No. 12)
Codon                             9  8  7  6  5  4  3  2  1
```

The resulting plasmid was designated pLSG24. Transformants harboring plasmid pLSG24 were identified by their AmpR phenotype and by hybridization with oligonucleotide DG118 (Seq ID No. 11).

EXAMPLE 5

Construction of Plasmids pLSG27 and pLS28

A. Construction of Plasmid pBSM:TthΔStuI/HindIII

Plasmids pLSG27 and pLSG28 are Tth Pol expression vectors that drive expression of a truncated form of Tth Pol. The truncation is an ~80 codon deletion from the amino-terminal-encoding region of the coding sequence for Tth Pol. To construct these vectors, plasmid pBSM:Tth5' was first digested to completion with restriction enzymes StuI and HindIII. The digested plasmid DNA was then treated with Klenow enzyme in the presence of all four dNTPs and recircularized by ligation. This treatment deleted the 5' noncoding region through codon 78 (the StuI site spans codons 77-79) of the Tth Pol gene. Plasmid pBSM:Tth5' also lacks the 3' end of the Tth Pol coding sequence. The resulting plasmid was designated pBSM:TthΔStuI/HindIII.

B. Construction of Plasmid pLSG25

Plasmid pBSM:TthΔStuI/HindIII was mutagenized with oligonucleotide DG191 (Seq ID No. 15) as described above to yield plasmid pLSG25. In plasmid pLSG25, the truncated Tth Pol coding sequence is placed in position for expression from the lac promoter. In addition, the lacZα coding sequence is deleted, and an AseI restriction enzyme recognition site is placed at the ATG start of the truncated coding sequence. The DG191 (Seq ID No. 15) mutagenizing linker has the following structure:

```
DG191   Seq ID No. 15   5'-CCTCCCCGCCTTGTAGGCCATTAATTT
                        GGTCTCCTGTGTGAAATTGTTATC-3'
```

Transformants harboring plasmid pLSG25 were identified by their AmpR phenotype and by hybridization with oligonucleotide DG193, which has the following structure:

DG193 Seq ID No. 16 5'-TTTGGTCTCCTGTGTG-3'

C. Construction of Plasmid pLSG26

Plasmid pLSG26 was constructed in the same manner as plasmid pLSG25, except that the mutagenizing linker was DG192 (Seq ID No. 17) as opposed to DG191 (Seq ID No. 15). DG192 (Seq ID No. 17) has the following structure:

```
DG192   Seq ID   5'-CCTCCCCGCCTTGTAGGCCAT-
        No. 17   ATGTTTGGTCTCCTGTGTGAAATTGTTATC-3'
```

Plasmid pLSG26 is identical to plasmid pLSG25, except that an NdeI, as opposed to AseI, restriction enzyme recognition site spans the ATG start codon of the truncated coding sequence. Transformants harboring plasmid pLSG26 were identified by their AmpR phenotype and by hybridization with oligonucleotide DG193 (Seq ID No. 16).

D. Final Construction of Plasmids pLSG27 and pLSG28

As noted above, plasmid pBSM:Tth5' lacks the 3' end of the Tth Pol coding sequence, so plasmids pLSG25 and pLSG26 also lack this sequence. To place this 3' end of the Tth Pol coding sequence in plasmids pLSG25 and pLSG26 in the correct reading frame, each plasmid was digested to completion with restriction enzymes BamHI and EcoRI. The large EcoRI-BamHI fragment of plasmid pLSG25 was then ligated with the ~1.2 kb BamHI-EcoRI restriction fragment of plasmid pLSG22 to yield plasmid pLSG27. The ~1.2 kb BamHI-EcoRI restriction fragment of plasmid pLSG22 contains the 3' end of the Tth Pol coding sequence. In a similar fashion, plasmid pLSG26 was digested with restriction enzymes BamHI and EcoRI and ligated with the ~1.2 kb BamHI-EcoRI restriction fragment of plasmid pLSG22 to yield plasmid pLSG28. Both plasmids pLSG27 and pLSG28 drive low level expression in *E. coli* of a truncated form of Tth Pol with polymerase activity.

EXAMPLE 6

Construction of Plasmids pLSG29 Through pLSG34

Although the lac promoter in plasmids pBSM:Tth, pLSG21, pLSG22, pLSG23, pLSG24, pLSG27, and pLSG28 drives expression of Tth Pol activity in *E. coli*, one of skill in the art recognizes that utilization of a stronger promoter than the lac promoter might increase Tth Pol expression levels. One well known, powerful promoter is the $P_L$ promoter from phage λ. In addition, higher expression levels and more efficient production can be achieved by altering the ribosome-binding site, transcription termination sequences, and origin of replication (or associated elements) of the Tth Pol expression vector. This example illustrates how such changes can be made by describing the construction of expression vectors in which the $\lambda P_L$ promoter and either the T7 or gene N ribosome-binding site are positioned for expression of Tth Pol.

A. Construction of Expression Vectors pDG160 and pDG161

Plasmid pDG160 is a $\lambda P_L$ cloning and expression vector that comprises the $\lambda P_L$ promoter and gene N ribosome-binding site (see U.S. Pat. No. 4,711,845, incorporated herein by reference), a restriction site polylinker positioned so that sequences cloned into the polylinker can be expressed under the control of the $\lambda P_L$-$N_{RBS}$, and a transcription terminator from the *Bacillus thuringiensis* delta-toxin gene (see U.S. Pat. No. 4,666,848, incorporated herein by reference). Plasmid pDG160 also carries a mutated RNAII gene, which renders the plasmid temperature sensitive for copy number (see U.S. Pat. No. 4,631,257, incorporated herein by reference).

These elements act in concert to make plasmid pDG160 a very useful and powerful expression vector. At 30°–32° C., the copy number of the plasmid is low, and in a host cell that carries a temperature-sensitive λ repressor gene, such as cI857, the $P_L$ promoter does not function. At 37°–41° C., however, the copy number of the plasmid is 50-fold higher than at 30°–32° C., and the cI857 repressor is inactivated, allowing the $P_L$ promoter to function. Plasmid pDG160 also carries an ampicillin resistance (AmpR) marker. Plasmid pDG161 is identical to plasmid pDG160, except the AmpR marker is replaced with a TetR (tetracycline resistance) marker.

So, plasmids pDG160 and pDG161 comprise the AmpR or TetR marker, the $λP_L$ promoter, the gene N ribosome-binding site, a polylinker, the BT cry PRE (BT positive retroregulatory element, U.S. Pat. No. 4,666,848) in a ColE11 $cop^{ts}$ vector. These plasmids were constructed from previously described plasmids and the duplex synthetic oligonucleotide linkers DG31 (Seq ID No. 18) and DG32 (Seq ID No. 19). The DG31/32 (Seq ID No. 18/Seq ID No. 18) duplex linker encodes a 5' HindIII cohesive end followed by SacI, NcoI, KpnI/Asp718, XmaI/SmaI recognition sites and a 3' BamHI cohesive end. This duplex linker is shown below.

with a portion of the DNA, and TetR colonies screened for presence of 4.2 kb plasmids. Several transformants were further screened by DNA restriction enzyme digestion and by sequence analysis of the polylinker region by the Sanger method. Several transformants contained a plasmid with the desired sequence, and the plasmid was designated pDG161.

B. Construction of Expression Plasmids pDG164 Through pDG181

To facilitate construction of Tth expression vectors and to increase the efficiency of translation initiation, plasmids pDG160 and pDG161 were altered to introduce changes in the $λP_L$ promoter and ribosome-binding site (RBS) region. In these alterations, plasmids pDG160 and pDG161 were digested with restriction enzymes BspMII and SacI and then ligated with short, synthetic linkers to create plasmids in which the small BspMI-SacI restriction fragment of plasmid pDG160 (or pDG161) was replaced with the duplex linker.

The duplex linkers used in these constructions had different structures and properties. Duplex DG106/DG107 (Seq ID No. 20/Seq ID No. 21) encodes the $T7_{RBS}$ and an NdeI enzyme recognition site at the ATG start codon and has the structure:

| Seq ID No. | | | |
|---|---|---|---|
| | | SacI  NcoI  KpnI  XmaI | |
| 18 | DG31 | 5'-AGCTTATGAGCTCCATGGTACCCCGGG | |
| 19 | | ATACTCGAGGTACCATGGGGCCCTAG-5' | DG32 |

This duplex linker and plasmid pFC54. t were used to construct plasmid pDG160.

Plasmid pFC54. t, a 5.96 kb plasmid described in U.S. Pat. No. 4,666,848, supra, and available in *E. coli* K12 strain DG95 carrying the prophage $λN_7N_{53}cI857$ $SusP_{80}$ from the ATCC under accession number ATCC 39789, was digested with restriction enzymes HindIII and BamHI, and the isolated vector fragment was ligated with a 5-fold molar excess of nonphosphorylated and annealed DG31/32 (Seq ID No. 18/Seq ID No. 19) duplex. Following ligation, the DNA was digested with XbaI (to inactivate the vector pFC54. t DNA fragment the linker replaces) and used to transform *E. coli* K 12 strain DG116 (ATCC 53,606) to ampicillin resistance. Colonies were screened by restriction enzyme digestion for loss of the des-ala-ser$^{125}$ IL-2 mutein sequence and acquisition of the DG31/32 (Seq ID No. 18/Seq ID No. 19) polylinker sequence. The polylinker region in the plasmid, designated pDG 160, of one AmpR transformant was sequenced to verify that the desired construction was achieved.

Plasmid pAW740CHB (available in *E. coli* strain K12 DG116 from the ATCC under accession number ATCC 67,605), the source of a modified tetracycline resistance gene in which the BamHI and HindIII restriction sites were eliminated, and which contains the $λP_L$ promoter gene N ribosome-binding site, and BT cry PRE in a ColE1 $cop^{ts}$ vector was digested to completion with restriction enzymes HindIII and BamHI and the 4.19 kb vector fragment purified by agarose gel electrophoresis. The purified vector DNA fragment was ligated with a 5-fold molar excess of nonphosphorylated annealed DG31/32 (Seq ID No. 18/Seq ID No. 19) duplex. *E. coli* K12 strain DG116 was transformed

| Seq ID No. | | | |
|---|---|---|---|
| | | | NdeI |
| 20 | DG106 | 5'-CCGGAAGAAGGAGATATACATATGAGCT-3' | |
| 21 | DG107 | 3'-TTCTTCCTCTATATGTATAC-5' | |

Duplex DG108/DG109 (Seq ID No. 22/Seq ID No. 23) encodes the $T7_{RBS}$ and an AseI restriction enzyme recognition site at the ATG start codon and has the structure:

| Seq ID No. | | |
|---|---|---|
| 22 | DG108 | 5'-CCGGAAGAAGGAGAAAAATTAATGAGCT-3' |
| 23 | DG109 | 3'-TTCTTCCTCTTTTTAATTAC-5' |

Duplex DG110/DG111 (Seq ID No. 24/Seq ID No. 25) encodes the $N_{RBS}$ and an NdeI restriction enzyme recognition site at the ATG start codon and has the structure:

| Seq ID No. | | |
|---|---|---|
| | | NdeI |
| 24 | DG110 | 5'-CCGGAGGAGAAAACATATGAGCT-3' |
| 25 | DG111 | 3'-TCCTCTTTTGTATAC-5' |

Duplex DG112/DG113 (Seq ID No. 26/Seq ID No. 27) encodes the $N_{RBS}$ and an AseI restriction enzyme recognition site at the ATG start codon and has the structure:

| Seq ID No. | | |
|---|---|---|
| | | AseI |
| 26 | DG112 | 5'-CCGGAGGAGAAAATTAATGAGCT-3' |
| 27 | DG113 | 3'-TCCTCTTTTAATTAC-5' |

The Duplexes and BspMII-SacI-digested plasmids pDG160 and pDG161 were ligated as shown in tabular form below to yield plasmids pDG164 through pDG171.

| BspMII-SacI Digested Vector | Duplex | Constructed Plasmid |
|---|---|---|
| pDG160 | DG106/DG107 | pDG164 |
| pDG160 | DG108/DG109 | pDG166 |
| pDG160 | DG110/DG111 | pDG168 |
| pDG160 | DG112/DG113 | pDG170 |
| pDG161 | DG106/DG107 | pDG165 |
| pDG161 | DG108/DG109 | pDG167 |
| pDG161 | DG110/DG111 | pDG169 |
| pDG161 | DG112/DG113 | pDG171 |

These vectors, together with plasmids pDG160 and pDG161, were also modified, prior to inserting the Tth Pol gene coding sequence, to yield plasmids pDG172 through pDG181.

This modification resulted in the destruction of the Csp45I (AsuII) restriction enzyme recognition site in plasmids pDG160, pDG161, and pDG164 through pDG171. Many of the vectors of the invention comprise a Csp45I site at the 5' end of the Tth Pol coding sequence. These Csp45I-deleted vectors serve as convenient vectors for cloning fragments generated with restriction enzyme Csp45I or AsuII. This Csp45I site is located in the colicin$^{IMM}$ gene of the plasmids and was deleted by digesting with restriction enzymes Csp45I, treating the Csp45I-digested DNA with Klenow enzyme in the presence of all four dNTPs to obtain blunt-ended, double-stranded DNA, and recircularizing the plasmid DNA by ligation. The resulting plasmids, designated pDG172 through pDG181, are shown in tabular form below.

| Starting Plasmid | Designation After Csp45I Site Removal |
|---|---|
| pDG160 | pDG172 |
| pDG161 | pDG173 |
| pDG164 | pDG174 |
| pDG165 | pDG175 |
| pDG166 | pDG176 |
| pDG167 | pDG177 |
| pDG168 | pDG178 |
| pDG169 | pDG179 |
| pDG170 | pDG180 |
| pDG171 | pDG181 |

Plasmids pDG172 through pDG181 were then used to place the Tth Pol gene of the present invention in frame for expression under the control of the $\lambda P_L$ promoter.

C. Construction of Tth Pol Expression Vectors pLSG29 Through pLSG36

The Tth Pol gene can be cloned into expression vectors pDG172 through pDG181 to create Tth Pol expression vectors. Several illustrative constructions are shown in tabular form below.

| Starting Plasmid | Source of Tth Pol Coding Sequence | Tth Pol Plasmid Expression |
|---|---|---|
| pDG174 | NdeI-BamHI Restriction Fragment of pLSG24 | pLSG31 |
| pDG174 | NdeI-BamHI Restriction Fragment of pLSG28 | pLSG35 |
| pDG175 | NdeI-BamHI Restriction Fragment of pLSG24 | pLSG32 |
| pDG177 | AseI-BamHI Restriction Fragment of pLSG23 | pLSG29 |
| pDG178 | NdeI-BamHI Restriction Fragment of pLSG24 | pLSG33 |
| pDG178 | NdeI-BamHI Restriction Fragment of pLSG28 | pLSG36 |
| pDG179 | NdeI-BamHI Restriction Fragment of pLSG24 | pLSG34 |
| pDG181 | AseI-BamHI Restriction Fragment of pLSG23 | pLSG30 |

Expression vectors pLSG29 through pLSG36 were transformed into E. coli K12 strain DG116 and cultured under conditions that allow for expression of Tth Pol. All transformants yielded about the same amounts of activity, although vectors with the $N_{RBS}$ may yield somewhat higher levels of activity than vectors with the $T7_{RBS}$. The $\lambda P_L$ promoter vectors also produced Tth Pol at levels at least an order of magnitude higher than the lac promoter expression vectors.

EXAMPLE 7

Synthesis of Recombinant Tth Pol Activity in *E. coli*

*E. coli* K12 strain DG116 (ATCC 53,606) harboring Tth Pol expression plasmids with the $\lambda P_L$ promoter is grown at 32° C. in Bonner-Vogel minimal salts media containing 0.5% glucose, 10 μg/ml thiamine, 0.25% (w/v) Difco casamino acids, and ampicillin (100 μg/ml) or tetracycline (10 μg/ml) as appropriate. Cells were grown to an $A_{600}$ of about 0.8 and shifted to 37° C. to derepress the $\lambda P_L$ promoter (inactivation of cI857 repressor) and increase the copy number of the ColE1 cop$^{rs}$ plasmid vector. After six to nine hours of growth at 37° C., aliquots of the cells were harvested, the cells centrifuged, and the pellets stored at −70° C.

Alternatively, *E. coli* K12 strain KB2 (ATCC 53,075) harboring a Tth expression plasmid was grown for eight hours at 32° C. in Bonner-Vogel minimal salts media containing 0.5% glucose, 5 μg/ml tryptophan, 10 μg/ml thiamine, 0.25% Difco casamino acids, and 100 μg/ml ampicillin or 10 μg/ml tetracycline to an $A_{600}$ of 3.0. Cells are harvested as above.

Cell pellets were resuspended to 5 to 10 O.D. units/ml in 50 mM Tris-Cl, pH 7.5, 1 mM EDTA, 2.4 mM PMSF, and 0.5 μg/ml leupeptin and lysed by sonication. Aliquots of the sonicated extracts were subjected to SDS-PAGE and analyzed by Coomassie staining and Western immunoblotting with rabbit polyclonal anti-Tth polymerase antibody. In addition, portions of the extracts were assayed in a high temperature (74° C.) DNA polymerase assay.

Western immunoblotting showed significant induction and synthesis of an approximately 94 kDa Tth DNA polymerase polypeptide in induced strains harboring Tth expression plasmids. Coomassie blue staining of SDS-PAGE-separated total cell protein revaled the presence of a new predominant protein at ~94 kDa in these induced strains. Finally, high temperature activity assays confirmed the significant level of recombinant Tth DNA polymerase synthesis in these *E. coli* strains.

EXAMPLE 8
PCR with Tth DNA Polymerase

About 1.25 units of the Tth DNA polymerase purified in Example 1 were used to amplify rRNA sequences from Tth genomic DNA. The reaction volume was 50 µl, and the reaction mixture contained 50 pmol of primer DG73 (Seq ID No. 28), $10^5$ to $10^6$ copies of the Tth genome (~$2 \times 10^5$ copies of genome/ng DNA), 50 pmol of primer DG74 (Seq ID No. 29), 200 µM of each dNTP, 2 mM $MgCl_2$, 10 mM Tris-HCl, pH 8.3, 50 mM KCl, and 100 µg/ml gelatin (although gelatin can be omitted).

The reaction was carried out on a Perkin Elmer DNA Thermal Cycler. Twenty to 30 cycles of 96° C. for 15 seconds; 50° C. for 30 seconds, and 75° C. for 30 seconds, were carried out. At 20 cycles, the amplification product (160 bp in size) could be faintly seen on an ethidium bromide stained gel, and at 30 cycles, the product was readily visible (under UV light) on the ethidium bromide stained gel.

The PCR may yield fewer non-specific products if fewer units(i.e. 0.31 U/50 µreaction) of Tth are used. In addition, the addition of a non-ionic detergent, such as laureth-12, to the reaction mixture to a final concentration of 1% can improve the yield of PCR product.

Primers DG73 (Seq ID No. 28) and DG74 (Seq ID No. 29) are shown below:

| Primer | Seq ID No. | Sequence |
|--------|------------|----------|
| DG73   | 28         | 5' TACGTTCCCGGGCCTTGTAC 3' |
| DG74   | 29         | 5' AGGAGGTGATCCAACCGCA 3'  |

---

We claim:

1. A purified, recombinantly produced enzyme preparation derived from *Thermus thermophilus* which has the following characteristics:

(1) it catalyzes the combination of nucleoside triphosphates to form a nucleic acid strand complementary to a template nucleotide sequence;

(2) it is thermostable;

(3) it has a temperature optimum for polymerization activity between 50° and 90° C.;

(4) it is able to function effectively in a polymerase chain reaction, wherein said reaction includes repeated exposure to a denaturation temperature of 90°–100° C.;

(5) it is free of nucleic acid encoding other *Thermus thermophilus* proteins;

(6) it is free of contaminating *Thermus thermophilus* proteins, and;

(7) wherein said enzyme contains an amino acid sequence selected from the group consisting of Seq ID No. 31, the sequence that is amino acids 10 to 834 of Seq ID No. 31, the sequence that is amino acids number 80 to 834 of Seq ID No. 31, and the sequence that is approximately amino acids number 279 to 834 of Seq ID No. 31.

2. The purified enzyme of claim 1 wherein said enzyme consists of amino acids 80–834 of Seq ID No. 31.

3. The purified enzyme of claim 1 wherein said enzyme consists of amino acids 10–834 of Seq ID No. 31.

4. The purified enzyme of claim 1 wherein said enzyme consists of amino acids 279–834 of Seq ID No. 31.

5. A recombinantly produced enzyme preparation derived from *Thermus thermophilus* which comprises a DNA polymerase and has the following characteristics:

(1) it catalyzes the combination of nucleoside triphosphates to form a nucleic acid strand complementary to a template nucleotide sequence;

(2) it is thermostable;

(3) it has a temperature optimum for polymerization activity between 50° and 90° C.;

(4) it is able to function effectively in a polymerase chain reaction, wherein said reaction includes repeated exposure to a denaturation temperature of 90°–100° C.;

(5) it has reverse transcriptase activity;

(6) it is free of nucleic acids encoding other *Thermus thermophilus* proteins; and (7) it is free of contaminating *Thermus thermophilus* proteins, wherein said DNA polymerase consists of an amino acid sequence that is SEQ ID NO: 31.

* * * * *

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GCGTGGCGGC GGAGGCGTTG 20

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CTTGGCGTCA AAGACCACGA TC 22

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GGCCTTGGGG CTTTCCAGA 19

( 2 ) INFORMATION FOR SEQ ID NO:4:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:4:

TGCGGGCCTG GATTGAGAAG                    20

( 2 ) INFORMATION FOR SEQ ID NO:5:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

CCCGGATCAG GTTCTCGTC                     19

( 2 ) INFORMATION FOR SEQ ID NO:6:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

GACCGGGGAC GAGTCCGAC                     19

( 2 ) INFORMATION FOR SEQ ID NO:7:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

CCGCTGTCCT GGCCCACATG                    20

( 2 ) INFORMATION FOR SEQ ID NO:8:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

TTCGGCCCAC CATGCCTGGT                    20

( 2 ) INFORMATION FOR SEQ ID NO:9:

( i ) SEQUENCE CHARACTERISTICS:
    ( A ) LENGTH: 41 base pairs
    ( B ) TYPE: nucleic acid
    ( C ) STRANDEDNESS: single (D) TOPOLOGY: linear (ii) MOLECULE TYPE: DNA (genomic)

(xi) SEQUENCE DESCRIPTION: SEQ ID NO:9:

CCTCTAAACG GCAGATCTGA TATCAACCCT TGGCGGAAAG C          41

(2) INFORMATION FOR SEQ ID NO:10:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:10:

CAGATCTGAT ATCAACCC          18

(2) INFORMATION FOR SEQ ID NO:11:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:11:

TGGTAACATA GCTTCCAT          18

(2) INFORMATION FOR SEQ ID NO:12:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:12:

TTCAAAGAGC GGAAGCATCG CCTCCAT          27

(2) INFORMATION FOR SEQ ID NO:13:

(i) SEQUENCE CHARACTERISTICS:
      (A) LENGTH: 61 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:13:

CCGGCCTTTG GGTTCGAATA ATGGTAACAT AGCTCCATT AATTGGGCC ACCTGTCCCC          60
G          61

(2) INFORMATION FOR SEQ ID NO:14:

(i) SEQUENCE CHARACTERISTICS:
      (A) LENGTH: 61 base pairs
      (B) TYPE: nucleic acid
      (C) STRANDEDNESS: single
      (D) TOPOLOGY: linear (ii) MOLECULE TYPE: DNA (genomic)

( x i ) SEQUENCE DESCRIPTION: SEQ ID NO:14:

CCGGCCTTTG GGTTCGAATA ATGGTAACAT AGCTTCCATA TGTTTGGGCC ACCTGTCCCC 60

G 61

( 2 ) INFORMATION FOR SEQ ID NO:15:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CCTCCCCGCC TTGTAGGCCA TTAATTTGGT CTCCTGTGTG AAATTGTTAT C 51

( 2 ) INFORMATION FOR SEQ ID NO:16:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

TTTGGTCTCC TGTGTG 16

( 2 ) INFORMATION FOR SEQ ID NO:17:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CCTCCCCGCC TTGTAGGCCA TATGTTTGGT CTCCTGTGTG AAATTGTTAT C 51

( 2 ) INFORMATION FOR SEQ ID NO:18:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

AGCTTATGAG CTCCATGGTA CCCCGGG 27

( 2 ) INFORMATION FOR SEQ ID NO:19:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

```
GATCCCCGGG GTACCATGGA GCTCATA                                                    27
```

( 2 ) INFORMATION FOR SEQ ID NO:20:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

```
CCGGAAGAAG GAGATATACA TATGAGCT                                                   28
```

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

```
CATATGTATA TCTCCTTCTT                                                            20
```

( 2 ) INFORMATION FOR SEQ ID NO:22:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

```
CCGGAAGAAG GAGAAAAATT AATGAGCT                                                   28
```

( 2 ) INFORMATION FOR SEQ ID NO:23:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
CATTAATTTT TCTCCTTCTT                                                            20
```

( 2 ) INFORMATION FOR SEQ ID NO:24:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
CCGGAGGAGA AAACATATGA GCT                                                        23
```

( 2 ) INFORMATION FOR SEQ ID NO:25:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:25:

CATATGTTTT CTCCT 15

( 2 ) INFORMATION FOR SEQ ID NO:26:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:26:

CCGGAGGAGA AAATTAATGA GCT 23

( 2 ) INFORMATION FOR SEQ ID NO:27:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:27:

CATTAATTTT CTCCT 15

( 2 ) INFORMATION FOR SEQ ID NO:28:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:28:

TACGTTCCCG GGCCTTGTAC 20

( 2 ) INFORMATION FOR SEQ ID NO:29:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:29:

AGGAGGTGAT CCAACCGCA 19

( 2 ) INFORMATION FOR SEQ ID NO:30:

( i ) SEQUENCE CHARACTERISTICS:
  ( A ) LENGTH: 2640 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:30:

| | | | | | |
|---|---|---|---|---|---|
| CCGAGGAGAC | CTACACCCCG | GAGGGCGTGC | GCTTCGCCCT | CCTCCTCCCC | AAGCCCGAGC | 60 |
| GGGAAGGTTT | CCTCAGGGCG | CTCCTGGACG | CCACCGGGG | ACAGGTGGCC | CTGGAGTAGC | 120 |
| ATGGAGGCGA | TGCTTCCGCT | CTTTGAACCC | AAAGGCCGGG | TCCTCCTGGT | GGACGGCCAC | 180 |
| CACCTGGCCT | ACCGCACCTT | CTTCGCCCTG | AAGGGCCTCA | CCACGAGCCG | GGGCGAACCG | 240 |
| GTGCAGGCGG | TCTACGGCTT | CGCCAAGAGC | CTCCTCAAGG | CCCTGAAGGA | GGACGGGTAC | 300 |
| AAGGCCGTCT | TCGTGGTCTT | TGACGCCAAG | GCCCCTCCT | TCCGCCACGA | GGCCTACGAG | 360 |
| GCCTACAAGG | CGGGGAGGGC | CCCGACCCCC | GAGGACTTCC | CCCGGCAGCT | CGCCCTCATC | 420 |
| AAGGAGCTGG | TGGACCTCCT | GGGGTTTACC | CGCCTCGAGG | TCCCCGGCTA | CGAGGCGGAC | 480 |
| GACGTTCTCG | CCACCCTGGC | CAAGAAGGCG | GAAAAGGAGG | GGTACGAGGT | GCGCATCCTC | 540 |
| ACCGCCGACC | GCGACCTCTA | CCAACTCGTC | TCCGACCGCG | TCGCCGTCCT | CCACCCCGAG | 600 |
| GGCCACCTCA | TCACCCCGGA | GTGGCTTTGG | GAGAAGTACG | GCCTCAGGCC | GGAGCAGTGG | 660 |
| GTGGACTTCC | GCGCCCTCGT | GGGGGACCCC | TCCGACAACC | TCCCCGGGGT | CAAGGGCATC | 720 |
| GGGGAGAAGA | CCGCCCTCAA | GCTCCTCAAG | GAGTGGGGAA | GCCTGGAAAA | CCTCCTCAAG | 780 |
| AACCTGGACC | GGGTAAAGCC | AGAAAACGTC | CGGGAGAAGA | TCAAGGCCCA | CCTGGAAGAC | 840 |
| CTCAGGCTCT | CCTTGGAGCT | CTCCCGGGTG | CGCACCGACC | TCCCCCTGGA | GGTGGACCTC | 900 |
| GCCCAGGGGC | GGGAGCCCGA | CCGGGAGGGG | CTTAGGGCCT | TCCTGGAGAG | GCTGGAGTTC | 960 |
| GGCAGCCTCC | TCCACGAGTT | CGGCCTCCTG | GAGGCCCCCG | CCCCCTGGA | GGAGGCCCCC | 1020 |
| TGGCCCCCGC | CGGAAGGGGC | CTTCGTGGGC | TTCGTCCTCT | CCCGCCCCGA | GCCCATGTGG | 1080 |
| GCGGAGCTTA | AAGCCCTGGC | CGCCTGCAGG | GACGGCCGGG | TGCACCGGGC | AGCAGACCCC | 1140 |
| TTGGCGGGGC | TAAAGGACCT | CAAGGAGGTC | CGGGGCCTCC | TCGCCAAGGA | CCTCGCCGTC | 1200 |
| TTGGCCTCGA | GGGAGGGGCT | AGACCTCGTG | CCCGGGACG | ACCCCATGCT | CCTCGCCTAC | 1260 |
| CTCCTGGACC | CCTCCAACAC | CACCCCCGAG | GGGGTGGCGC | GGCGCTACGG | GGGGAGTGG | 1320 |
| ACGGAGGACG | CCGCCCACCG | GGCCCTCCTC | TCGGAGAGGC | TCCATCGGAA | CCTCCTTAAG | 1380 |
| CGCCTCGAGG | GGGAGGAGAA | GCTCCTTTGG | CTCTACCACG | AGGTGGAAAA | GCCCCTCTCC | 1440 |
| CGGGTCCTGG | CCCACATGGA | GGCCACCGGG | GTACGGCTGG | ACGTGGCCTA | CCTTCAGGCC | 1500 |
| CTTTCCCTGG | AGCTTGCGGA | GGAGATCCGC | CGCCTCGAGG | AGGAGGTCTT | CCGCTTGGCG | 1560 |
| GGCCACCCCT | TCAACCTCAA | CTCCCGGGAC | CAGCTGGAAA | GGGTGCTCTT | TGACGAGCTT | 1620 |
| AGGCTTCCCG | CCTTGGGGAA | GACGCAAAAG | ACAGGCAAGC | GCTCCACCAG | CGCCGCGGTG | 1680 |
| CTGGAGGCCC | TACGGGAGGC | CCACCCCATC | GTGGAGAAGA | TCCTCCAGCA | CCGGGAGCTC | 1740 |
| ACCAAGCTCA | AGAACACCTA | CGTGGACCCC | CTCCCAAGCC | TCGTCCACCC | GAGGACGGGC | 1800 |
| CGCCTCCACA | CCCGCTTCAA | CCAGACGGCC | ACGGCCACGG | GGAGGCTTAG | TAGCTCCGAC | 1860 |
| CCCAACCTGC | AGAACATCCC | CGTCCGCACC | CCCTTGGGCC | AGAGGATCCG | CCGGGCCTTC | 1920 |
| GTGGCCGAGG | CGGGTTGGGC | GTTGGTGGCC | CTGGACTATA | GCCAGATAGA | GCTCCGCGTC | 1980 |
| CTCGCCCACC | TCTCCGGGGA | CGAAAACCTG | ATCAGGGTCT | TCCAGGAGGG | GAAGGACATC | 2040 |
| CACACCCAGA | CCGCAAGCTG | GATGTTCGGC | GTCCCCCGG | AGGCCGTGGA | CCCCCTGATG | 2100 |
| CGCCGGGCGG | CCAAGACGGT | GAACTTCGGC | GTCCTCTACG | GCATGTCCGC | CCATAGGCTC | 2160 |
| TCCCAGGAGC | TTGCCATCCC | CTACGAGGAG | GCGGTGGCCT | TTATAGAGCG | CTACTTCCAA | 2220 |
| AGCTTCCCCA | AGGTGCGGGC | CTGGATAGAA | AAGACCCTGG | AGGAGGGGAG | GAAGCGGGGC | 2280 |

```
TACGTGGAAA CCCTCTTCGG AAGAAGGCGC TACGTGCCCG ACCTCAACGC CGGGGTGAAG    2340

AGCGTCAGGG AGGCCGCGGA GCGCATGGCC TTCAACATGC CCGTCCAGGG CACCGCCGCC    2400

GACCTCATGA AGCTCGCCAT GGTGAAGCTC TTCCCCCGCC TCCGGGAGAT GGGGGCCCGC    2460

ATGCTCCTCC AGGTCCACGA CGAGCTCCTC CTGGAGGCCC CCCAAGCGCG GGCCGAGGAG    2520

GTGGCGGCTT TGGCCAAGGA GGCCATGGAG AAGGCCTATC CCCTCGCCGT GCCCCTGGAG    2580

GTGGAGGTGG GGATGGGGGA GGACTGGCTT TCCGCCAAGG GTTAGGG GGGCCCTGCCGTT    2640
```

( 2 ) INFORMATION FOR SEQ ID NO:31:

( i ) SEQUENCE CHARACTERISTICS:
        ( A ) LENGTH: 834 amino acids
        ( B ) TYPE: amino acid
        ( C ) STRANDEDNESS: single
        ( D ) TOPOLOGY: linear ( i i ) MOLECULE TYPE:

( x i ) SEQUENCE DESCRIPTION: SEQ ID NO:31:

```
Met Glu Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285
```

```
Leu Leu Glu Ala Pro Ala Pro Leu Glu Glu Ala Pro Trp Pro Pro Pro
    290             295                 300
Glu Gly Ala Phe Val Gly Phe Val Leu Ser Arg Pro Glu Pro Met Trp
305             310                 315                 320
Ala Glu Leu Lys Ala Leu Ala Ala Cys Arg Asp Gly Arg Val His Arg
                325             330                 335
Ala Ala Asp Pro Leu Ala Gly Leu Lys Asp Leu Lys Glu Val Arg Gly
            340             345                 350
Leu Leu Ala Lys Asp Leu Ala Val Leu Ala Ser Arg Glu Gly Leu Asp
        355             360                 365
Leu Val Pro Gly Asp Asp Pro Met Leu Leu Ala Tyr Leu Leu Asp Pro
    370             375                 380
Ser Asn Thr Thr Pro Glu Gly Val Ala Arg Arg Tyr Gly Gly Glu Trp
385             390                 395                 400
Thr Glu Asp Ala Ala His Arg Ala Leu Leu Ser Glu Arg Leu His Arg
                405             410                 415
Asn Leu Leu Lys Arg Leu Glu Gly Glu Lys Leu Leu Trp Leu Tyr
            420             425                 430
His Glu Val Glu Lys Pro Leu Ser Arg Val Leu Ala His Met Glu Ala
        435             440                 445
Thr Gly Val Arg Leu Asp Val Ala Tyr Leu Gln Ala Leu Ser Leu Glu
    450             455                 460
Leu Ala Glu Glu Ile Arg Arg Leu Glu Glu Val Phe Arg Leu Ala
465             470                 475                 480
Gly His Pro Phe Asn Leu Asn Ser Arg Asp Gln Leu Glu Arg Val Leu
                485             490                 495
Phe Asp Glu Leu Arg Leu Pro Ala Leu Gly Lys Thr Gln Lys Thr Gly
            500             505                 510
Lys Arg Ser Thr Ser Ala Ala Val Leu Glu Ala Leu Arg Glu Ala His
        515             520                 525
Pro Ile Val Glu Lys Ile Leu Gln His Arg Glu Leu Thr Lys Leu Lys
    530             535                 540
Asn Thr Tyr Val Asp Pro Leu Pro Ser Leu Val His Pro Arg Thr Gly
545             550                 555                 560
Arg Leu His Thr Arg Phe Asn Gln Thr Ala Thr Ala Thr Gly Arg Leu
                565             570                 575
Ser Ser Ser Asp Pro Asn Leu Gln Asn Ile Pro Val Arg Thr Pro Leu
            580             585                 590
Gly Gln Arg Ile Arg Arg Ala Phe Val Ala Glu Ala Gly Trp Ala Leu
        595             600                 605
Val Ala Leu Asp Tyr Ser Gln Ile Glu Leu Arg Val Leu Ala His Leu
    610             615                 620
Ser Gly Asp Glu Asn Leu Ile Arg Val Phe Gln Glu Gly Lys Asp Ile
625             630                 635                 640
His Thr Gln Thr Ala Ser Trp Met Phe Gly Val Pro Pro Glu Ala Val
                645             650                 655
Asp Pro Leu Met Arg Arg Ala Ala Lys Thr Val Asn Phe Gly Val Leu
            660             665                 670
Tyr Gly Met Ser Ala His Arg Leu Ser Gln Glu Leu Ala Ile Pro Tyr
        675             680                 685
Glu Glu Ala Val Ala Phe Ile Glu Arg Tyr Phe Gln Ser Phe Pro Lys
    690             695                 700
Val Arg Ala Trp Ile Glu Lys Thr Leu Glu Glu Gly Arg Lys Arg Gly
705             710                 715                 720
```

| | | | | | | | | | | | | | | |
|---|---|---|---|---|---|---|---|---|---|---|---|---|---|---|
| Tyr | Val | Glu | Thr | Leu 725 | Phe | Gly | Arg | Arg | Arg 730 | Tyr | Val | Pro | Asp | Leu 735 | Asn |
| Ala | Arg | Val | Lys 740 | Ser | Val | Arg | Glu | Ala 745 | Ala | Glu | Arg | Met | Ala 750 | Phe | Asn |
| Met | Pro | Val 755 | Gln | Gly | Thr | Ala | Ala 760 | Asp | Leu | Met | Lys | Leu 765 | Ala | Met | Val |
| Lys | Leu 770 | Phe | Pro | Arg | Leu | Arg 775 | Glu | Met | Gly | Ala | Arg 780 | Met | Leu | Leu | Gln |
| Val 785 | His | Asp | Glu | Leu | Leu 790 | Leu | Glu | Ala | Pro | Gln 795 | Ala | Arg | Ala | Glu | Glu 800 |
| Val | Ala | Ala | Leu | Ala 805 | Lys | Glu | Ala | Met | Glu 810 | Lys | Ala | Tyr | Pro | Leu 815 | Ala |
| Val | Pro | Leu | Glu 820 | Val | Glu | Val | Gly | Met 825 | Gly | Glu | Asp | Trp | Leu 830 | Ser | Ala |
| Lys | Gly | | | | | | | | | | | | | | |